US009976140B2

(12) United States Patent
Tseng et al.

(10) Patent No.: US 9,976,140 B2
(45) Date of Patent: May 22, 2018

(54) MICRORNA AND USES IN BROWN FAT DIFFERENTIATION

(71) Applicant: Joslin Diabetes Center, Inc., Boston, MA (US)

(72) Inventors: Yu-Hua Tseng, Newton, MA (US); Hongbin Zhang, Allston, MA (US)

(73) Assignee: Joslin Diabetes Center, Inc., Boston, MA (US)

(*) Notice: Subject to any disclaimer, the term of this patent is extended or adjusted under 35 U.S.C. 154(b) by 0 days. days.

(21) Appl. No.: 14/896,787

(22) PCT Filed: Jun. 13, 2014

(86) PCT No.: PCT/US2014/042227
§ 371 (c)(1),
(2) Date: Dec. 8, 2015

(87) PCT Pub. No.: WO2014/201314
PCT Pub. Date: Dec. 18, 2014

(65) Prior Publication Data
US 2016/0138017 A1    May 19, 2016

Related U.S. Application Data

(60) Provisional application No. 61/835,018, filed on Jun. 14, 2013.

(51) Int. Cl.
*A61K 48/00* (2006.01)
*C07H 21/02* (2006.01)
*C12N 15/113* (2010.01)
*A61K 31/517* (2006.01)
*C12N 5/077* (2010.01)

(52) U.S. Cl.
CPC .......... *C12N 15/113* (2013.01); *A61K 31/517* (2013.01); *C12N 5/0653* (2013.01); *C12N 2310/141* (2013.01); *C12N 2320/30* (2013.01)

(58) Field of Classification Search
CPC ..... A61K 48/00; A61K 31/713; C12N 15/113
See application file for complete search history.

(56) References Cited

U.S. PATENT DOCUMENTS 9,416,369 B2 * 8/2016 Ruohola-Baker ........ C12N 9/22
2012/0122959 A1   5/2012 Stoffel et al.

FOREIGN PATENT DOCUMENTS

| WO | 2007112754 A2 | 10/2007 | |
|---|---|---|---|
| WO | WO 2009/043353 A2 * | 4/2009 | ......... C12N 2310/11 |
| WO | WO 2009/150839 A1 * | 12/2009 | ......... C12N 2310/11 |
| WO | WO 2011/138457 A1 * | 11/2011 | ........... C12N 15/113 |

OTHER PUBLICATIONS

Schirle, et al. "The Crystal Structure of Human Argonaute 2" Science; May 25, 2012; vol. 336; No. 6084; pp. 1037-1040.
Guo, et al. "Mammalian microRNAs predominantly act to decrease target mRNA levels" Nature; Aug. 12, 2010; vol. 466; No. 7308; pp. 835-840.
Djuranovic, et al. "A parsimonious model for gene regulation by miRNAs" Science; Feb. 4, 2011; vol. 4; No. 331, pp. 550-553.
Zheng, et al. "Interaction with factor inhibiting HIF-1 defines an additional mode of cross-coupling between the Notch end hypoxia signaling pathways" PNAS; Mar. 4, 2008; vol. 105; No. 9; pp. 3368-3373.
Lando, et al. "FIH-1 is an asparaginly hydroxylase enzyme that regulates the transcriptional activity of hypoxia-inducible factor" Genes & Development; 2002; vol. 16; pp. 1466-1471.
Devries, et al. "Consequences of IkappaB a;pha hydroxylation by the factor inhibiting HIF (FIH)" FEBS Letters; Dec. 1, 2010; vol. 584; No. 23; pp. 4725-4730.
Zhang, et al. "The asparaginyl hydroxylase FIH (Factor Inhibiting HIF) is an essential regulator of metabolism" Cell Metab.; May 5, 2010; vol. 11; No. 5; pp. 364-378.
Rochford, et al. "ETO/MTG8 is an inhibitor of C/EBPbeta activity and a regulator of early adipogenesis" Molecular and Cellular Biology; Nov. 2002; vol. 24; No. 22; pp. 9863-9872.
Wu, et al. "Mechanisms Controlling Mitochondrial Biogenesis and Respiration through the Thermogenic Coactivator PGC-1" Cell; Jul. 9, 1999; pp. 115-124.
Ahmadian, et al. "Desnutrin/ATGL is Regulated by AMPK and is Required for a Brown Adipose Phenotype" Cell Metab.; Jun. 8, 2011; vol. 13; No. 6; pp. 739-748.
Puigserver, et al. "A Cold-Inducible Coactivator of Nuclear Receptors Linked to Adaptive Thermogenesis" Cell; Mar. 20, 1998; vol 92; pp. 829-839.
Wu, et al. "Mechanisms Controlling Mitochondrial Biogenesis and Respiration through the Thermogenic Coactivator PGC-1" Cell; Jul. 9, 1999; vol. 98; pp. 115-124.
Cao, et al. "p38 Mitogen-Activated Protein Kinase is the Central Regulator of Cyclic AMP-Dependent Transcription of the Brown Fat Uncoupling Protein 1 Gene" Molecular and Cellular Biology; Apr. 2004; vol. 24; No. 7; pp. 3057-3067.
Tseng, et al. "New role of bone morphogenetic protein 7 in brown adipogenesis and energy expenditure" Nature; Aug. 21, 2008; vol. 454; No. 7202; pp. 1000-1004.
Schulz, et al. "Identification of inducible brown adipocyte progenitors residing in skeletal muscle and white fat" PNAS; Jan. 4, 2011; vol. 108; No. 1; pp. 143-148.
Yin, et al. "MicroRNA-133 Controls Brown Adipose Determination in Skeletal Muscle Satellite Cells by Targeting Prdm16" Cell Metab.; Feb. 5, 2013; vol. 17; No. 2; pp. 210-224.

(Continued)

*Primary Examiner* — Amy H Bowman
(74) *Attorney, Agent, or Firm* — Pierce Atwood LLP; Kevin M. Farrell; David J. Wilson

(57) ABSTRACT

This invention reveals a novel miRNA and a novel miRNA-regulated signaling network which controls brown adipogenesis and thermogenic programs, thereby providing a powerful approach for the treatment of obesity and related metabolic diseases. In this regard, the present invention is also directed towards methods of treatment of obesity and excess weight (overweight) and metabolic disorders caused by or aggravated by a subject being overweight or obese.

18 Claims, 19 Drawing Sheets

(56) References Cited

OTHER PUBLICATIONS

Sun, et al. "MiR-193b-365, a brown fat enriched microRNA cluster, is essential for brown fat differentiation" Nat. Cell Biol.; Feb. 1, 2012; vol. 13; No. 8; pp. 958-965.
Mori, et al. "Essential Role for miR0196a in Brown Adipogenesis of White Fat Progenitor Cells" PLOS Biology; Apr. 2012; vol. 10; Issue 4; pp. 1-15.
Mann, et al. "miRNA-based mechanism for the commitment of multipotent progenitors to a single cellular fate" PNAS; Sep. 7, 2010; vol. 107; No. 36; pp. 15804-15809.
Kajimoto, et al. "MicroRNA and 3T3-L1 pre-adipocyte differentiation" RNA; 2006; vol. 12; pp. 1626-1632.
Tseng, et al. "Prediction of preadipocyte differentiation by gene expression reveals role of insulin receptor substrates and necdin" Nature Cell Biology; Jun. 2005; vol. 7; No. 6; pp. 601-611 with 3 supplementary information pages.
Kim, et al. "miR-27a is a negative regulator of adipocyte differentiation via suppressing PPARgama expression" Biochemical and Biophysical Research Communication; 2010; vol. 392; pp. 323-328.
Trajkovski, et al. "MyomiR-133 regulates brown fat differentiation through Prdm16" Nature Cell Biology; Dec. 2012; vol. 14; No. 12; pp. 1330-1338 with 7 pages of supplementary information.

* cited by examiner

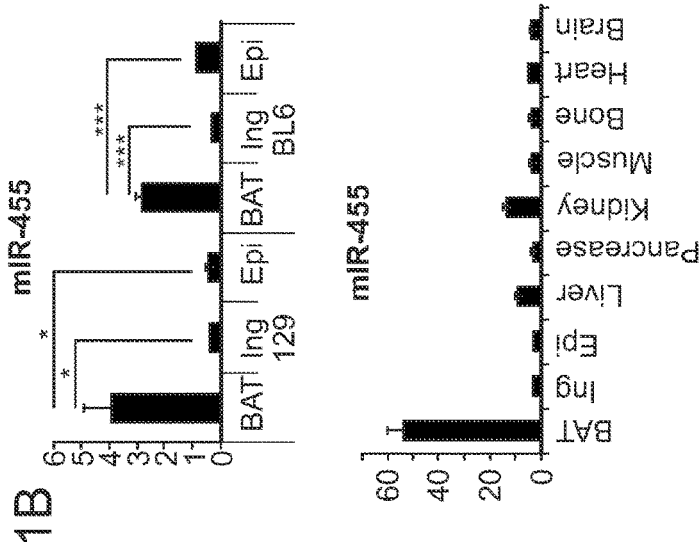
FIG. 1A
FIG. 1B
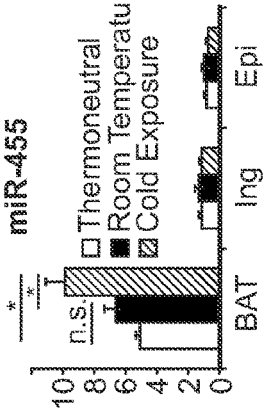
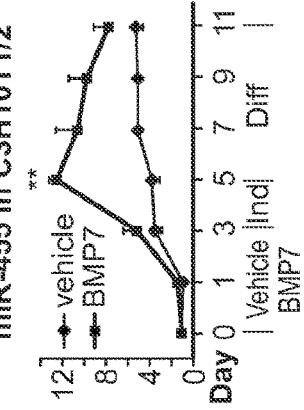
FIG. 1E
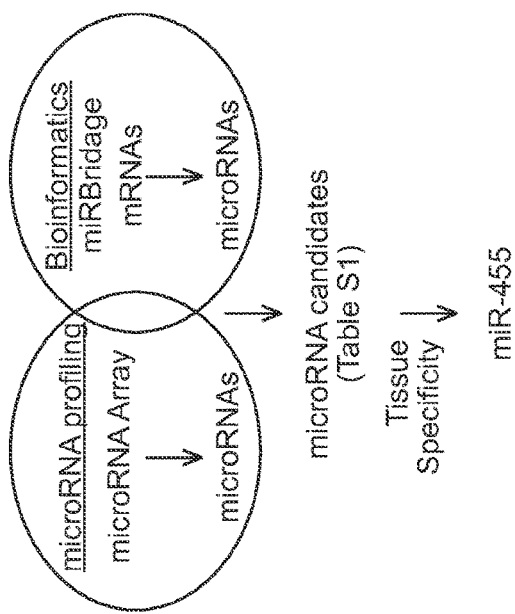
FIG. 1C
FIG. 1D
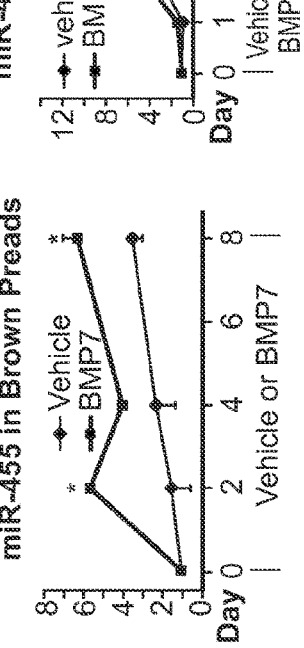

FIG. 2G
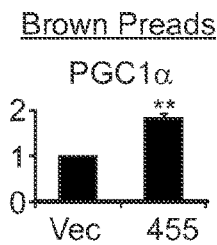 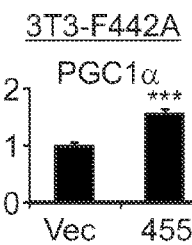 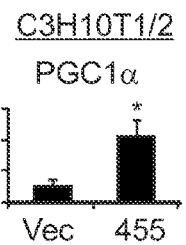

FIG. 6

| microRNAs | Known Function or Signaling |
|---|---|
| miR-153 | Neuronal development |
| miR-9 | Neuronal development |
| miR-17-5p/20/93/106/519d | BMP signaling-mediated myocardial differentiation |
| miR-1/206 | Skeletal muscle development |
| miR-24 | Tumorigenesis |
| miR-192/215 | Involved in TGF-b/BMP/Smad-regulated Chronical Kidney Disease |
| miR-455 | Expression in brown adipose tissue |
| miR-93/291-3p/294/295/302/372/373/520 | Biomarker of fibrosis Enhanes angiogenesis |
| miR-199 | BMP-mediated mciroRNA procesing |
| miR-33 | Cholestoeral transport |
| miR-25/32/92/363/367 | Targets TNF-related apoptosis inducing ligand (TRAIL) death receptor-4 and promotes apoptosis resistance in cholangiocarcinoma |
| miR-7 | miR-7a egulation of Pax6 controls spatial origin of forebrain dopaminergic neurons. |
| miR-205 | Controls osteogenic lineage progression by targeting transcription factor Runx2. |

| miR-455 Target Genes | Seed region position in 3'UTR | Pairing of target region (top) and miRNA (bottom) |
|---|---|---|
| HIF1an | HIF1an 3'UTR Position 106-112<br><br>mmu-miR-455 | [SEQ ID NO: 8]<br>5'...GCACGCUGCACUUAAUGGACUGG...3'<br>                    \|\|\|\|\|\|\|<br>3'     CACAUAUACGGGCACCUGACG 5'<br>[SEQ ID NO: 9] |
| | HIF1an 3'UTR Position 1610-1617<br><br>mmu-miR-455 | [SEQ ID NO: 10]<br>5'...GCUUACAGGCCCCAUGGACUGA...3'<br>                  \|\|\|\|\|\|\|\|<br>3'     CACAUAUACGGGCACCUGACG 5'<br>[SEQ ID NO: 11] |

FIG. 8A

| | | |
|---|---|---|
| necdin | necdin 3' UTR Position 430-436 | 5'...auccAUGUG-GAAUGGACUGa...3' [SEQ ID NO: 12]<br>　　　　　　｜｜:｜｜　｜｜｜｜｜｜｜｜<br>3'　cacaUAUACGGGCACCUGACg 5' [SEQ ID NO: 13] |
| | mmu-miR-455 | |
| | necdin 3' UTR Position 445-451 | 5'...acugAUUUGAAC-UGGACUGu...3' [SEQ ID NO: 14]<br>　　　　　　｜｜　｜｜　｜｜｜｜｜｜｜｜<br>3'　cacaUAUACGGGCACCUGACg 5' [SEQ ID NO: 15] |
| | mmu-miR-455 | |
| Runx1t1 | Runx1t1 3' UTR Position 3666-3672 | 5'...UUUUUUUCCUUAGUUGGACUGU...3' [SEQ ID NO: 16]<br>　　　　　　　　　　　｜｜｜｜｜｜｜｜<br>3'　　CACAUAUACGGGCACCUGACG 5' [SEQ ID NO: 17] |
| | mmu-miR-455 | |

FIG. 8B

FIG. 13
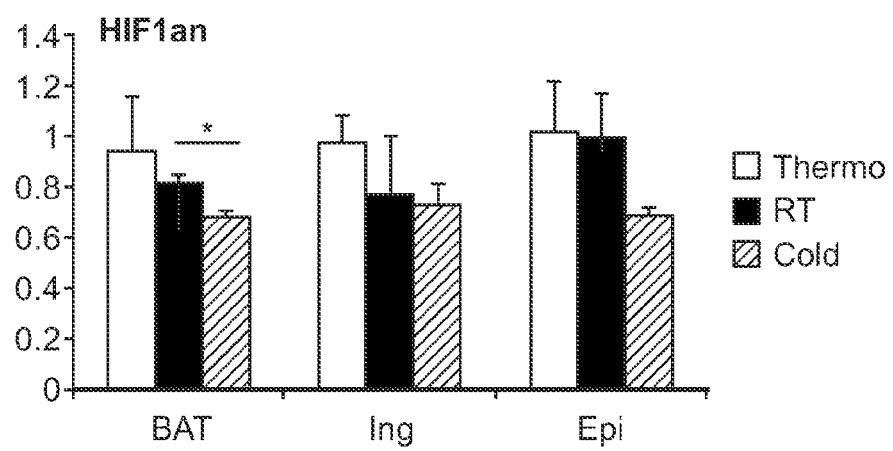
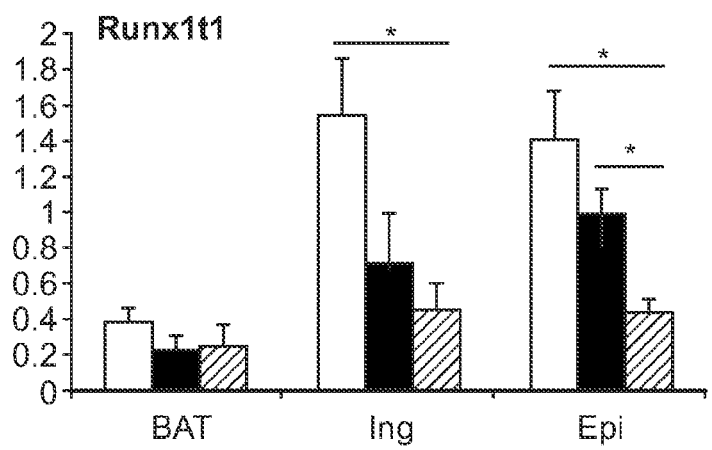
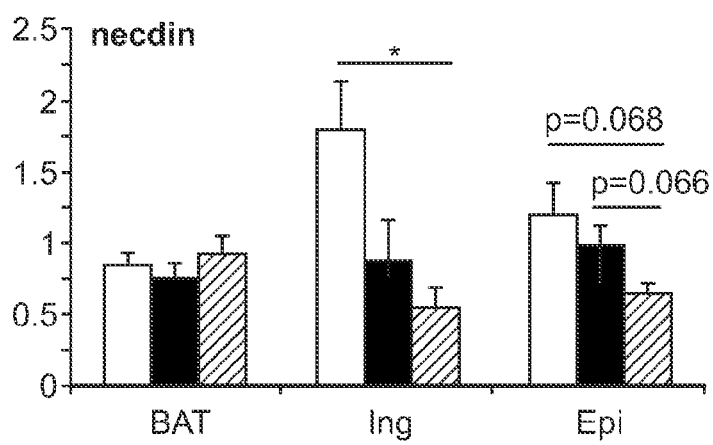

FIG. 16

| Specie | Gene ID | RNA Sequence GeneBank Accession | miRbase Accession | mature miR-455 sequence (5'→3') | |
|---|---|---|---|---|---|
| Human | 619556 | NR_030255 | MI0003513 | gcaguccaUgggcauauacac | SEQ ID NO: 1 |
| mouse | 735262 | NR_030477 | MI0004679 | gcaguccaCgggcauauacac | SEQ ID NO: 2 |
| Rattus norvegicus (Norway rat) | 100314205 | NR_032279 | MI0006148 | gcaguccacgggcauauacacU | SEQ ID NO: 3 |
| Gallus gallus (chicken) | 777905 | NR_031554 | MI0003707 | ugcaguccaugggcauauacac | SEQ ID NO: 4 | miR-455 (mouse) LNA mimic sequence miR-455 mimic guide strand seq  rG*rC*rA*rG*rU*rC*rC*rA*rC*rG*rG*rG*rC*rA*rU*rA*rU*rA*rC*rA*rC   SEQ ID NO: 5 miR-455 passenger strand seq  TArUrGrUrGrCrCrUrUrUrGrGrArCrUrArCrA*rU*rG   SEQ ID NO: 6 miR-455 LNA inhibitor seq  TATGCCCGTGGACTG   SEQ ID NO: 7

MICRORNA AND USES IN BROWN FAT DIFFERENTIATION

This invention was made with government support under grant number R01DK077097 awarded by NIH. The government has certain rights in the invention.

SEQUENCE LISTING

The instant application contains a Sequence Listing which has been submitted electronically in ASCII format and is hereby incorporated by reference in its entirety. Said ASCII copy, created on Nov. 30, 2016, is named W5889950.txt and is 3,121 Bytes in size.

BACKGROUND

Obesity has become a world-spreading disorder, causing type 2 diabetes, cardiovascular disease and cancers, among numerous other medical conditions. Of the two types of adipocytes, white adipocytes are specialized in energy storage and brown adipocytes are specialized in thermogenic energy expenditure. Cannon and Nedergaard, Physiol Rev 2004, 84(1):277. Recently, it was demonstrated that human adults have functional brown adipose tissue (BAT) (Celi, et al., N. Eng. J. Med. (2009) 360(15): 1509), raising the possibility of counteracting obesity through enhancing the activity and development of brown adipocytes. Obesity is caused by an excess amount of body fat, i.e., white adipose tissue. Brown adipose tissue dissipates chemical energy as heat and can counteract obesity. What is needed in the art are compositions and methods for the activation and promotion of BAT cells and activity in subjects in need of treatment for obesity and related disorders.

SUMMARY OF THE INVENTION

Provided herein are compositions and methods for the treatment of obesity and related disorders through the promotion of brown adipose tissue activation and differentiation. microRNAs (miRNAs) are emerging as key regulators in development and disease. Combining miRNA array and mirBridge bioinformatic analysis, a number of miRNAs were identified by the inventors that are instrumental in the regulation of brown adipogenesis. A novel microRNA, herein referred to as miR-455, exhibits a BAT-specific expression pattern and is induced by cold exposure. In vitro gain-of-function and loss-of-function studies show that miR-455 regulates UCP1 expression and brown adipocyte differentiation in multipotent progenitor cells and committed brown preadipocytes. Transgenic mice overexpressing miR-455 in adipose tissue display marked browning of subcutaneous white fat. The inventors demonstrate that miR-455 targets hypoxia inducible factor 1 alpha subunit inhibitor (HIF1an), a hydroxylase which interacts with AMP-activated protein kinase alpha 1 subunit (AMPKα1) and inhibits its activity. Thus, miR-455 activates AMPKα1 by suppressing HIF1an and AMPK in turn acts as a metabolic trigger to initiate mitochondria biogenesis, PGC1α induction and brown adipogenesis. Concomitantly, miR-455 also targets adipogenic suppressor Runx1t1 and necdin, allowing the initiation of adipogenic program.

This invention reveals a novel miRNA and a novel miRNA-regulated signaling network which controls brown adipogenesis and thermogenic programs, thereby providing a powerful approach for the treatment of obesity and related metabolic diseases. In this regard, the present invention is also directed towards methods of treatment of obesity and excess weight (overweight) and metabolic disorders caused by or aggravated by a subject being overweight or obese. These metabolic disorders are described in detail below but can include diabetes, insulin sensitivity, insulin resistance, glucose intolerance, etc. The methods disclosed herein include the administration of the novel miRNA of the present invention (and compositions comprising the novel miRNA of the present invention) to subjects in need of treatment for being overweight or obese and/or for metabolic conditions stemming from being overweight or obese, which are detailed below. Further, the present invention contemplates methods of treatment for subjects that are overweight or obese and metabolic disorders stemming from being overweight or obese by inhibiting downstream components of the signaling pathways that are inhibited by the miRNA of the present invention.

DESCRIPTION OF THE FIGURES

FIG. 1 shows the identification of microRNAs mediating BMP7-induced brown adipogenesis. a, microRNA array was performed on C3H10T1/2 cells treated with vehicle or BMP7. mRNA array were performed on RNA samples from 3 sets of cells: C3H10T1/2 cells treated with vehicle vs. BMP7, primary Sca-1$^+$ cells treated with vehicle vs. BMP7, and SVFs from 129 vs. C57B/L6 mice. The gene sets from the 3 mRNA arrays were subjected to miRBridge analysis to identify 3 categories of microRNA. microRNA candidates were identified as those appeared in top 20 of at least 2 categories in miRBridge analysis and also significantly regulated by BMP7 in the microRNA array (S. Table 1). These microRNAs were then examined for their brown fat specificity. b, miR-455 expression in different tissues (n=5-6). c-d, miR-455 expression during differentiation of brown preadipocytes (c) and C3H10T1/2 (d) cells. Shown is a representative of 4 independent experiments. e, C57B/L6 mice were maintained at room temperature, 30° C. (thermoneutral) or 4° C. (cold) for 48 hours, miR-455 expression was quantified by Q-RT-PCR (n=6). (*$p<0.05$, $p<0.01$, *$p<0.001$, n.s., non-significant).

FIG. 6 shows microRNA candidates identified in microRNA array coupled with miRBridge bioinformatic analysis based on mRNA arrays.

FIG. 8 shows the miR-455 target sequences in the 3'UTR of target genes.

FIG. 13 shows cold exposure of mice (as in FIG. 1e) suppressed the expression of miR-455 target genes in adipose tissues.

FIG. 16 shows oligonucleotide sequences of the present invention.

DETAILED DESCRIPTION OF THE INVENTION

Figure 2A:
FIG. 2 shows miR-455 overexpression induced brown adipogenesis in vitro. All the cells were transduced by lentiviral vectors. Stably transduced cells were selected and pooled (see methods). a-b, Brown adipocytes overexpressing. miR-455 on day 17. Oil O staining (a) and brown adipocyte marker gene expression by Q-RT-PCR (b). c-d, 3T3-F442A (white) adipocytes (on day 8) were incubated with 100 uM Norepinephrine (NE) for 4 hours. Oil Red O stained (c) and Q-RT-PCR analysis of brown adipocyte gene (d). e-f, C3H10T1/2 adipocytes overexpressing miR-455 (day 8). Oil O staining (e) and Q-RT-PCR of brown adipocyte gene expression (f). g, Q-RT-PCR analysis of PGC1α in brown and 3T3-F442A (white) preadipocytes, and undifferentiated C3H10T1/2 fibroblasts overexpressing miR-455. h, Ratio of DNA content between mito-gene (COXII) and nuclear gene (globin) quantified by Q-PCR (upper panel), and bioenergetic profile analysis by Seahorse (lower Panel) in undifferentiated C3H10T1/2 cells. i, RT-Q-PCR analysis of lypolytic and fatty acid mobilization genes in brown and white preadipocytes overexpressing miR-455. Shown are representative of 3 to 5 independent experiments with each performed in triplicates or quadruplicates (* $p<0.05$, ** $p<0.01$, #$p<10^{-6}$).

The present invention relates to a method of upregulating Brown Adipose Tissue (BAT) in a subject, the method comprising contacting one or more cells in the subject, the cells selected from brown adipose cells, white adipose cells and preadipocytes with a composition comprising one or more exogenous miRNA-455 selected from the group consisting of [SEQ ID NOs: 1-4] (see, FIG. 16). The miRNA-455 of the present invention may be modified, shortened, lengthened or otherwise changed, by methods known to one of ordinary skill in the art, while still being a miRNA of the present invention, so long as the modified miRNA-455 functions similarly to the unmodified sequence. Exemplary modifications and associated methods are given below. Administration of the miRNA of the present invention is by any method known to one of ordinary skill in the art. In this regard, the miRNA of the present invention may be formulated into a compound by methods known to one of ordinary skill in the art, to aid in the administration and/or uptake by the body, and/or entry to and into target cells and tissues. Exemplary methods and compositions suitable for the formulation of the miRNA into an administratable formula are given below.

The upregulation of BAT refers to inducing or initiating an increase in BAT differentiation from, for example, preadipocytes and white adipose tissue (WAT). The upregulation of BAT may also include the increase in the activity of preexisting BAT cells wherein the preexisting BAT cells become more thermogenicly active. As BAT cells become more active they produce heat by utilizing the body's energy stores. The upregulation of BAT may include both increases in BAT cell number and BAT cell activity.

The subject for treatment may be an overweight or obese individual. Obesity and overweight are terms known in the art and are defined below. The subject for treatment may also have, either concurrent with obesity or being overweight, or independent from obesity or being overweight, diabetes. The diabetes may be type 1 or type 2 diabetes.

The present invention also includes upregulating BAT by contacting BAT cells (and, optionally, WAT and preadipocytes) with an agent that inhibits at least partially one or more of HIF1an, Rux1+1 and necdin. These proteins are shown herein to mediate the effects of miRNA-455 on BAT, WAT and preadipocytes. miRNA-455 is inhibitory of these proteins. Thus, the inhibition of any one of more of these three proteins results in the upregulation of BAT differentiation and activity (see, for example, the Exemplification section below). One suitable agent for the inhibition of HIF1an is Clioquinol (CQ: Iodochlorhydroxyquin or 5-chloro-7-iodo-8-hydroxyquinoline). Other suitable inhibitors of HIF1an, Rux1+1 and necdin that are known to one of ordinary skill in the art and are included herein.

The present invention further relates to methods and compositions for the treatment of obesity (and excessive weight, i.e., being overweight but not obese) in a subject. The invention contemplates a composition suitable for treatment of obesity comprising one or more exogenous miRNA-455 selected from the group consisting of [SEQ ID NOs: 1-4](see, FIG. 16). The miRNA-455 of the present invention may be modified, shortened, lengthened or otherwise changed, by methods known to one of ordinary skill in the art, while still being a miRNA of the present invention, so long as the modified miRNA-455 functions similarly to the unmodified sequence. Exemplary modifications and associated methods are given below. Administration of the miRNA of the present invention is by any method known to one of ordinary skill in the art. In this regard, the miRNA of the present invention may be formulated into a compound by methods known to one of ordinary skill in the art, to aid in the administration and/or uptake by the body, and/or entry to and into target cells and tissues. Exemplary methods and compositions suitable for the formulation of the miRNA into an administratable formula are given below.

The method of the treatment of obesity by the present invention results in increasing the thermogenic activity of BAT in a subject, increasing the amount of BAT in the subject, or both. The subject for treatment may also have diabetes. The diabetes may be type 1 or type 2 diabetes.

The present invention also contemplates a method for treating obesity (and excessive weight, i.e., being overweight but not obese) in a subject comprising contacting one or more cells in the subject with an agent that inhibits at least partially one or more of HIF1an, Rux1+1 and necdin, the cells selected from brown adipose cells, white adipose cells and preadipocytes. One suitable agent for the inhibition of HIF1an is Clioquinol (CQ: Iodochlorhydroxyquin or 5-chloro-7-iodo-8-hydroxyquinoline). Other suitable inhibitors of HIF1an, Rux1+1 and necdin that are known to one of ordinary skill in the art and are included herein.

Unless defined otherwise, all technical and scientific terms used herein have the same meaning as is commonly understood by one of skill in the arts to which the invention belongs. Unless specific definitions are provided, the nomenclature utilized in connection with, and the procedures and techniques of analytical chemistry, synthetic organic chemistry, and medicinal and pharmaceutical chemistry described herein are those well known and commonly used in the art. In the event that there is a plurality of definitions for terms herein, those in this section prevail. Standard techniques may be used for chemical synthesis, chemical analysis, pharmaceutical preparation, formulation and delivery, and treatment of subjects. Certain such techniques and procedures may be found for example in "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

DEFINITIONS

"Blood glucose level" means the concentration of glucose in the blood of a subject. In certain embodiments, blood glucose levels are expressed as milligrams of glucose per deciliter of blood. In certain embodiments, blood glucose levels are expressed as mmol of glucose per liter of blood.

"Elevated blood glucose level" means a blood glucose level that is higher than normal, as defined by those of ordinary skill in the art.

"Fasted blood glucose level" means a blood glucose level after a subject has fasted for a certain length of time. For example, a subject may fast for at least 8 hours prior to measurement of a fasted blood glucose level.

"Post-prandial blood glucose level" means a blood glucose level after a subject has eaten a meal. In certain embodiments, a post-prandial blood glucose level is measured two hours after a subject has eaten a meal.

"Whole blood glucose level" means the concentration of glucose in whole blood which has not been subjected to separation.

"Plasma blood glucose level" means the concentration of glucose in plasma following separation of whole blood into plasma and red blood cell fractions.

"Insulin sensitivity" means the ability of cells to take up glucose in response to insulin action.

"Insulin resistance" means a condition in which normal amounts of insulin are inadequate to produce a normal insulin response from fat, muscle and liver cells. Insulin resistance in fat cells results in hydrolysis of stored triglycerides, which elevates free fatty acids in the blood. Insulin resistance in muscle reduces the uptake of glucose from the blood by muscle cells. Insulin resistance in liver reduces glucose storage and a failure to suppress glucose production. Elevated free fatty acids, reduced glucose uptake, and elevated glucose production all contribute to elevated blood glucose levels. High plasma levels of insulin and glucose due to insulin resistance often leads to metabolic syndrome and type 2 diabetes.

"Improving insulin resistance" means increasing the ability of cells to produce a normal insulin response. In certain embodiments, insulin resistance is improved in muscle cells, leading to an increased uptake of glucose in muscle cells. In certain embodiments, insulin resistance is improved in liver cells, leading to increased glucose storage in liver cells. In certain embodiments, insulin resistance is improved in fat cells, leading to reduced hydrolysis of triglycerides, and consequently reduced free fatty acid in the blood.

"Metabolic disorder" means a condition characterized by an alteration or disturbance in one or more metabolic processes in the body. Metabolic disorders include, but are not limited to, hyperglycemia, prediabetes, diabetes, type 1 diabetes, type 2 diabetes, obesity, diabetic dyslipidemia, metabolic syndrome, and hyperinsulinemia. "Diabetes" or "diabetes mellitus" means a disease in which the body does not produce or properly use insulin, resulting in abnormally high blood glucose levels. In certain embodiments, diabetes is type 1 diabetes. In certain embodiments, diabetes is type 2 diabetes.

"Prediabetes" means a condition in which a subject's blood glucose levels are higher than in a subject with normal blood glucose levels but lower but not high enough for a diagnosis of diabetes.

"Type 1 diabetes" means diabetes characterized by loss of the insulin-producing beta cells of the islets of Langerhans in the pancreas leading to a deficiency of insulin (also known as insulin-dependent diabetes mellitus or IDDM). Type I diabetes can affect children or adults, but typically appears between the ages of 10 and 16.

"Type 2 diabetes" means diabetes characterized by insulin resistance and relative insulin deficiency (also known as diabetes mellitus type 2, and formerly called diabetes mellitus type 2, non-insulin-dependent diabetes (NIDDM), obesity related diabetes, or adult-onset diabetes).

"Obesity" means an excessively high amount of body fat or adipose tissue in relation to lean body mass. The amount of body fat (or adiposity) includes both the distribution of fat throughout the body and the size of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese. "Overweight" refers to individuals with a BMI of 25 to 30, as defined by the Center for Disease Control and Prevention.

"Metabolic syndrome" means a condition characterized by a clustering of lipid and nonlipid risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Steatosis" means a condition characterized by the excessive accumulation of triglycerides in hepatocytes.

"Steatohepatitis" means steatosis with inflammation.

"Glucose Tolerance Test" or "GTT" means a test performed to determine how quickly glucose is cleared from the blood. Typically, the test involves administration of glucose, followed by measurement of glucose levels in blood at intervals over a period of time. "IPGTT" means a GTT performed following intraperitoneal injection of glucose. "OGTT" means a GTT performed following oral administration of glucose. In certain embodiments, a GTT is used to test for pre-diabetes. In certain embodiments, a GTT is used to identify a subject with diabetes. In certain embodiments, a GTT is used to identify a subject at risk for developing diabetes. In certain embodiments a GTT is used to identify a subject having insulin resistance.

"Insulin Tolerance Test (ITT)" means a test performed to measure insulin sensitivity through hormone response to the stress of a low blood sugar level. In certain embodiments, a ITT is used to test or pre-diabetes. In certain embodiments, a ITT is used to identify a subject with diabetes. In certain embodiments, a ITT is used to identify a subject at risk for developing diabetes. In certain embodiments a ITT is used to identify a subject having insulin resistance.

"Metabolic rate" means the rate of metabolism or the amount of energy expended in a given period. "Basal metabolic rate" means the amount of energy expended while at rest in a neutrally temperate environment, in the post-absorptive state (meaning that the digestive system is inactive, which requires about twelve hours of fasting in humans); the release of energy in this state is sufficient only for the functioning of the vital organs, such as the heart, lungs, brain and the rest of the nervous system, liver, kidneys, sex organs, muscles and skin.

"Anti-miR" means an oligonucleotide having a nucleobase sequence complementary to a microRNA. In certain embodiments, an anti-miR is a modified oligonucleotide.

"Subject" means a human or non-human animal selected for treatment or therapy.

"Subject in need thereof" means a subject identified as in need of a therapy or treatment.

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, or intramuscular administration.

"Subcutaneous administration" means administration just below the skin.

"Intravenous administration" means administration into a vein.

"Administered concomitantly" refers to the administration of at least two agents to a subject in any manner in which the pharmacological effects of both are manifest in the subject at the same time. Concomitant administration does not require that both agents be administered in a single pharmaceutical composition, in the same dosage form, or by the same route of administration. The time during which the effects of the agents occur need not be identical. The effects need only be overlapping for a period of time and need not be coextensive. "Duration" means the period of time during which an activity or event continues. In certain embodiments, the duration of treatment is the period of time during which doses of a pharmaceutical agent or pharmaceutical composition are administered.

"Therapy" means a disease treatment method. In certain embodiments, therapy includes, but is not limited to, chemotherapy, surgical resection, liver transplant, and/or chemoembolization.

"Treatment" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Upregulate" means to induce an increase in the targeted substance or action.

"At risk for developing" means a subject is predisposed to developing a condition or disease. In certain embodiments, a subject at risk for developing a condition or disease exhibits one or more symptoms of the condition or disease, but does not exhibit a sufficient number of symptoms to be diagnosed with the condition or disease. In certain embodiments, a subject at risk for developing a condition or disease exhibits one or more symptoms of the condition or disease, but to a lesser extent required to be diagnosed with the condition or disease.

"Prevent the onset of" means to prevent the development a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

"Therapeutic agent" means a pharmaceutical agent used for the cure, amelioration or prevention of a disease.

"Dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Therapeutically effective amount" refers to an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a sterile aqueous solution.

"Pharmaceutical agent" means a substance that provides a therapeutic effect when administered to a subject.

"Active pharmaceutical ingredient" means the substance in a pharmaceutical composition that provides a desired effect.

"Acceptable safety profile" means a pattern of side effects that is within clinically acceptable limits.

"Side effect" means a physiological response attributable to a treatment other than desired effects.

"Injection site reaction" means inflammation or abnormal redness of skin at a site of injection in an individual.

"Subject compliance" means adherence to a recommended or prescribed therapy by a subject.

"Comply" means the adherence with a recommended therapy by a subject.

"Recommended therapy" means a treatment recommended by a medical professional for the treatment, amelioration, or prevention of a disease.

"Target nucleic acid" means a nucleic acid to which an oligomeric compound is designed to hybridize.

"Targeting" means the process of design and selection of nucleobase sequence that will hybridize to a target nucleic acid.

"Targeted to" means having a nucleobase sequence that will allow hybridization to a target nucleic acid.

"Modulation" means to a perturbation of function or activity. In certain embodiments, modulation means an increase in gene expression. In certain embodiments, modulation means a decrease in gene expression.

"Expression" means any functions and steps by which a gene's coded information is converted into structures present and operating in a cell.

"5' target site" refers to the nucleobase of a target nucleic acid which is complementary to the 5'-most nucleobase of a particular oligonucleotide.

"3' target site" means the nucleobase of a target nucleic acid which is complementary to the 3'-most nucleobase of a particular oligonucleotide.

"Region" means a portion of linked nucleosides within a nucleic acid.

"Segment" means a smaller or sub-portion of a region.

"Nucleobase sequence" means the order of contiguous nucleobases, in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that an oligomeric compound is capable of hybridizing to a target nucleic acid under stringent hybridization conditions.

"Fully complementary" means each nucleobase of an oligomeric compound is capable of pairing a nucleobase at each corresponding position in a target nucleic acid. For example, in certain embodiments, an oligomeric compound wherein each nucleobase has complementarity to a nucleobase within a region of a miRNA stem-loop sequence is fully complementary to the miRNA stem-loop sequence.

"Percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound. In certain embodiments, percent complementarity of an means the number of nucleobases that are complementary to the target nucleic acid, divided by the length of the modified oligonucleotide.

"Percent identity" means the number of nucleobases in first nucleic acid that are identical to nucleobases at corresponding positions in a second nucleic acid, divided by the total number of nucleobases in the first nucleic acid.

"Hybridize" means the annealing of complementary nucleic acids that occurs through nucleobase complementarity.

"Mismatch" means a nucleobase of a first nucleic acid that is not capable of pairing with a nucleobase at a corresponding position of a second nucleic acid.

"Identical" means having the same nucleobase sequence.

miRNA

A microRNA (abbr. miRNA) is a small non-coding RNA molecule (ca. 22 nucleotides) found in plants and animals, which functions in transcriptional and post-transcriptional regulation of gene expression. Encoded by eukaryotic nuclear DNA, miRNAs function via base-pairing with complementary sequences within mRNA molecules, usually resulting in gene silencing via translational repression or target degradation. The human genome may encode over 1000 miRNAs, which may target about 60% of mammalian genes and are abundant in many human cell types. See, en.wikipedia.org/wiki/MicroRNA. The miRNA of the present invention is also referred to as an oligonucleotide herein.

Metabolic Disorders

Metabolic disorders are characterized by one or more abnormalities in metabolic function in the body. Certain metabolic disorders are related to defects in how the body uses blood glucose, resulting in abnormally high levels of blood glucose. Metabolic disorders may also be characterized by a deficiency in insulin production, or a deficiency in sensitivity to insulin. Metabolic disorders affect millions of people worldwide, and can be life-threatening disorders. Obesity is a metabolic disorder, a symptom of metabolic disorders and an inducer of other metabolic disorders. Many metabolic disorders are the result of or aggravated by being overweight or obese. As such, there is a need for method and compositions to treat, prevent, or delay the onset of metabolic disorders by treating, preventing or delaying the onset of excess weight in a subject.

As illustrated herein, the administration of oligonucleotides of miRNA-455 (e.g., one or more of [SEQ ID NOs: 1-4]) resulted in increases of BAT activation and differentiation thereby promoting improved blood glucose levels, decreased gluconeogenesis, enhanced insulin sensitivity, and decreased plasma cholesterol. These effects were observed in animal models. It is also contemplated that continued administration of the compounds of the present invention will result in a decrease in body weight, which is due to a decrease in body fat.

Administration of a compound comprising an oligonucleotide sequence of [(e.g., one or more of [SEQ ID NOS: 1-4]) may further result in one or more clinically desirable outcomes. Such clinically desirable outcomes include but are not limited to reduced blood glucose levels, reduced HbA1c levels, improved glucose tolerance, improved insulin resistance and reduced gluconeogenesis, and/or decreased obesity, as a result of increased BAT differentiation and/or BAT activity.

Accordingly, provided herein are methods and compositions to increase BAT differentiation and activation or activity and thereby reduce blood glucose levels, decrease gluconeogenesis and improve insulin sensitivity. Also provided herein are methods to treat, prevent, or delay the onset of metabolic disorders that are related to obesity, elevated blood glucose levels, increased gluconeogenesis and impaired insulin sensitivity. In certain embodiments, metabolic disorders include, but are not limited to, prediabetes, diabetes, including Type 1 or Type 2 diabetes, metabolic syndrome, obesity, diabetic dyslipidemia, hyperglycemia, hypoglycemia, and hyperinsulinemia. Treatment in a subject comprises administering to the subject a compound comprising an oligonucleotide (miRNA) consisting of sequences of the present invention, or an effective portion or fragment thereof or modified version thereof.

In certain embodiments, the methods provided herein comprise measuring blood glucose levels. Blood glucose levels may be measured before and/or after administration of a compound of the present invention, as described herein. Blood glucose levels may be measured in whole blood, or may be measured in plasma. Blood glucose levels may be measured in a clinical laboratory, or may be measured using a blood glucose meter.

In certain embodiments, blood glucose levels are measured in a subject when the subject has fasted for at least 8 hours. In certain embodiments, blood glucose levels are measured at random times, and the measurement is not timed according to the intake of food or drink. In certain embodiments, blood glucose levels are measured in the post-prandial state, i.e., after the subject has eaten a meal. In certain embodiments, blood glucose levels are measured in a subject two hours after the subject has eaten a meal. In certain embodiments, blood glucose levels are measured at timed intervals following administration of glucose to the subject, in order to determine how quickly the subject's body clears glucose from the blood. Any measurements of blood glucose levels may be made in whole blood or in plasma.

In certain embodiments, the subject has elevated blood glucose levels. In certain embodiments, a subject is identified as having elevated blood glucose levels. Such identification is typically made by a medical professional, and by standards that are known to one of ordinary skill in the art. In certain embodiments, an elevated blood glucose levels is a fasting blood glucose level between 100 and 125 mg/dL. In certain embodiments, an elevated blood glucose level is a fasting blood glucose level above 126 mg/dL. In certain embodiments, an elevated blood glucose level is a two-hour post-prandial glucose level between 140 and 199 mg/dL. In certain embodiments, an elevated blood glucose level is a two-hour post-prandial glucose level at 200 mg/dL or higher.

In certain embodiments, a subject having elevated blood glucose levels has pre-diabetes. In certain embodiments, a subject is identified as having pre-diabetes. In certain such embodiments, the subject has a fasting blood glucose level between 100 and 125 mg/dL. In certain such embodiments, the subject has a two-hour post-prandial blood glucose level between 140 and 199 mg/dL. A diagnosis of pre-diabetes is typically made by a medical professional, who may consider factors in addition to blood glucose levels when determining whether a subject has pre-diabetes, and by standards that are known to one of ordinary skill in the art.

In certain embodiments, a subject having elevated blood glucose levels has diabetes. In certain embodiments, a subject is identified as having diabetes according to the subject's blood glucose levels. In certain such embodiments, the subject has a fasting blood glucose level above 126 mg/dL. In certain such embodiments, the subject has a two-hour post-prandial blood glucose level at or above 200 mg/dL. A diagnosis of diabetes is typically made by a medical professional, who may consider factors in addition to blood glucose levels when determining whether a subject has diabetes, and by standards that are known to one of ordinary skill in the art.

In certain embodiments, the method provided herein comprise monitoring blood glucose levels before administration of a compound comprising an oligonucleotide of the present invention. In certain embodiments, a subject measures blood glucose levels one or more times daily.

In certain embodiments, methods for reducing blood glucose levels comprise reducing a subject's blood glucose levels to blood glucose levels determined as desirable by medical organizations, such as the American Diabetes Association or the World Health Organization, as are known by one of ordinary skill in the art. In certain embodiments, blood glucose levels are reduced below 130 mg/dL when measured before a subject has had a meal. In certain embodiments, blood glucose levels are reduced to below 180 mg/dL when measured after a subject has had a meal.

In certain embodiments, the administration occurs at least once per week. In certain embodiments, the administration occurs once every two weeks. In certain embodiments, the administration occurs once every three weeks. In certain embodiments, the administration occurs once every four weeks. The frequency of administration may be set by a medical professional to achieve a desirable blood glucose level in a subject. The frequency of administration may be dependent upon a subject's blood glucose levels. For example, in certain embodiments, administration may be more frequent when a subject has elevated blood glucose levels.

Measurements of HbA1c levels may be used to determine how well a subject's blood glucose levels are controlled over time, as is known to one of ordinary skill in the art. HbA1c levels are an indication of the amount of glycated hemoglobin in the blood, and can provide an estimate of how well a subject's blood glucose levels have been managed over 2-3 month period prior to the measurement of HbA1c levels. High HbA1c levels may put a subject at risk for developing complications related to diabetes, such as eye disease, heart disease, kidney disease, nerve damage, or stroke. As such, in certain embodiments it is desirable that a subject's HbA1c levels be within ranges that are considered normal by a medical professional. In certain embodiments, an HbA1c level of 6% or less is normal. In certain embodiments, a medical professional may recommend that a subject's HbA1c level be 7% or less. In certain embodiments, the administering results in reduced HbA1c levels.

In certain embodiments, a subject having elevated blood glucose levels is insulin resistant. One of the main functions of insulin is to lower blood glucose levels. A subject whose cells are sensitive to the effects of insulin needs only a relatively small amount of insulin to keep blood glucose levels in the normal range. A subject who is insulin resistant requires more insulin to get the same blood glucose-lowering effects. Insulin resistance may cause hyperinsulinemia. Hyperinsulinemia may be associated with high blood pressure, heart disease and heart failure, obesity (particularly abdominal obesity), osteoporosis, and certain types of cancer, such as colon, breast and prostate cancer.

Insulin resistance may be detected using a procedure known as the hyperinsulinemic euglycemic clamp, which measures the amount of glucose necessary to compensate for an increased insulin level without causing hypoglycemia. During the procedure, insulin is infused at 10-120 mU per m.sup.2 per minute. In order to compensate for the insulin infusion, a 20% solution of glucose is infused to maintain blood sugar levels between 5 and 5.5 mmol/L. The rate of glucose infusion is determined by checking the blood sugar levels every 5 to 10 minutes. Low-dose insulin infusions are more useful for assessing the response of the liver, whereas high-dose insulin infusions are useful for assessing peripheral (i.e., muscle and fat) insulin action. The rate of glucose infusion during the last 30 minutes of the test determines insulin sensitivity. If high levels (7.5 mg/min or higher) are required, the subject is insulin-sensitive. Very low levels (4.0 mg/min or lower) indicate that the subject is resistant to insulin action. Levels between 4.0 and 7.5 mg/min are not definitive and suggest impaired glucose tolerance. Impaired glucose tolerance may be an early sign of insulin resistance. Glucose tracers, such as 3-$^3$H glucose, 6,6 $^2$H-glucose, or 1-$^{13}$C glucose, may be used in the procedure. Other radioactive forms of glucose may be employed in a research setting. Prior to beginning the hyperinsulinemic period, a 3 hour tracer infusion enables the determination of the basal rate of glucose production. During the clamp procedure, the plasma tracer concentrations enable the calculation of whole-body insulin-stimulated glucose metabolism, as well as the production of glucose by the body (i.e., endogenous glucose production).

In certain embodiments, provided herein are methods for improving insulin resistance in a subject comprising administering a subject to the subject a compound comprising an oligonucleotide consisting of, for example, one or more of [SEQ ID NOs: 1-4], or modified versions or effective fractions thereof. In certain embodiments, the subject has insulin resistance. In certain embodiments, the methods comprise selecting a subject having insulin resistance.

In certain embodiments, provided herein are methods for improving insulin resistance in a subject comprising administering a subject to the subject a compound comprising an oligonucleotide consisting of 7 to 12 linked nucleosides of [SEQ ID NOs: 1-4], or modified versions thereof. In certain embodiments, a subject having elevated blood glucose levels has insulin resistance.

In certain embodiments, a subject having diabetes has insulin resistance. In certain embodiments, a subject having type 2 diabetes has insulin resistance. In certain embodiments, a subject having type 1 diabetes has insulin resistance.

In certain embodiments, provided herein are methods for reducing gluconeogenesis in a subject comprising administering a subject to the subject a compound comprising an oligonucleotide consisting of [SEQ ID NOs: 1-4], or effective or modified fractions thereof. In certain embodiments, the subject has elevated gluconeogenesis. In certain embodiments, the subject is identified as having elevated gluconeogenesis. In certain embodiments, the administering results in a reduction in gluconeogenesis. In certain embodiments, a pyruvate tolerance test is used to measure gluconeogenesis in a subject. In certain embodiments, blood glucose levels are used to measure gluconeogenesis in a subject. In certain embodiments, the rate of gluconeogenesis is measured in a subject. In certain embodiments, a reduction in gluconeogenesis is a reduction in the rate of gluconeogenesis. In certain embodiments, the rate of gluconeogenesis is measured in the subject prior to administration. In certain embodiments, the rate of gluconeogenesis is measured in the subject after administration.

In certain embodiments, provided herein are methods for treating a metabolic disorder in a subject comprising administering to the subject a administering a subject to the subject a compound comprising an oligonucleotide consisting of (e.g., one or more of [SEQ ID NOS: 1-4]), or an effective fraction or modified version thereof. In certain embodiments, the subject has a metabolic disorder. In certain embodiments, the subject is identified as having a metabolic disorder. In certain embodiments, a metabolic disorder includes, without limitation, prediabetes, diabetes (including Type 1 or Type 2 diabetes), metabolic syndrome, obesity, or diabetic dyslipidemia, hyperglycemia, hypoglycemia, and hyperinsulinemia. In certain embodiments, the subject is diagnosed with one or more metabolic disorders. A subject may be diagnosed with a metabolic disorder following the administration of medical tests well-known to those in the medical profession.

In certain embodiments, provided herein are methods for treating a metabolic disorder in a subject comprising administering to the subject a compound comprising an oligonucleotide consisting of 7 to 12 linked nucleosides and having a nucleobase sequence of, e.g., one or more of [SEQ ID NOS: 1-4].

In certain embodiments, provided herein are methods for preventing the onset of a metabolic disorder in a subject comprising administering to the subject a administering a subject to the subject a compound comprising an oligonucleotide consisting of (e.g., one or more of [SEQ ID NOS: 1-4]), or an effective fraction thereof. In certain embodiments, the subject is at risk for developing a metabolic disorder. In certain embodiments, the subject is identified being at risk for developing a metabolic disorder. In certain embodiments, a metabolic disorder is prediabetes, diabetes (including Type 1 or Type 2 diabetes), metabolic syndrome, obesity, or diabetic dyslipidemia, hyperglycemia, hypoglycemia, hyperinsulinemia, ketoacidosis and celiac disease.

In certain embodiments, provided herein are methods for preventing the onset of a metabolic disorder in a subject comprising administering to the subject a compound comprising an oligonucleotide consisting of 7 to 12 linked nucleosides of, e.g., one or more of [SEQ ID NOS: 1-4].

In certain embodiments, provided herein are methods for delaying the onset of a metabolic disorder in a subject comprising administering to the subject a compound comprising administering to the subject a administering a subject to the subject a compound comprising an oligonucleotide consisting of, e.g., one or more of [SEQ ID NOs: 1-4], or an effective fraction thereof. In certain embodiments, the subject is at risk for developing a metabolic disorder. In certain embodiments, the subject is identified being at risk for developing a metabolic disorder. In certain embodiments, a metabolic disorder includes, without limitation, prediabetes, diabetes (including Type 1 or Type 2 diabetes), metabolic syndrome, obesity, or diabetic dyslipidemia, hyperglycemia, hypoglycemia, and hyperinsulinemia.

In certain embodiments, provided herein are methods for delaying the onset of a metabolic disorder in a subject comprising administering to the subject a compound comprising an oligonucleotide consisting of 7 to 12 linked nucleosides of, e.g., one or more of [SEQ ID NOs: 1-4].

In certain embodiments, a subject has one or more metabolic disorders. In certain embodiments, a subject has been diagnosed with one or more metabolic disorders. A subject may be diagnosed with a metabolic disorder following the administration of medical tests well-known to those in the medical profession.

A subject's response to treatment may be evaluated by tests similar to those used to diagnosis the metabolic disorder, including blood glucose level tests, glucose tolerance tests, and HbA1c tests. Response to treatment may also be assessed by comparing post-treatment test results to pre-treatment test results.

Compounds

The compounds provided herein are useful for the treatment of metabolic disorders including obesity and excess weight (i.e., overweight). In certain embodiments, the compound comprises an oligonucleotide. In certain such embodiments, the compound consists of an oligonucleotide. In certain embodiments, the oligonucleotide is a modified oligonucleotide.

In certain such embodiments, the compound comprises an oligonucleotide hybridized to a complementary strand, i.e., the compound comprises a double-stranded oligomeric compound. In certain embodiments, the hybridization of an oligonucleotide to a complementary strand forms at least one blunt end. In certain such embodiments, the hybridization of an oligonucleotide to a complementary strand forms a blunt end at each terminus of the double-stranded oligomeric compound. In certain embodiments, a terminus of an oligonucleotide comprises one or more additional linked nucleosides relative to the number of linked nucleosides of the complementary strand. In certain embodiments, the one or more additional nucleosides are at the 5' terminus of an oligonucleotide. In certain embodiments, the one or more additional nucleosides are at the 3' terminus of an oligonucleotide. In certain embodiments, at least one nucleobase of a nucleoside of the one or more additional nucleosides is complementary to the target RNA. In certain embodiments, each nucleobase of each one or more additional nucleosides is complementary to the target RNA. In certain embodiments, a terminus of the complementary strand comprises one or more additional linked nucleosides relative to the number of linked nucleosides of an oligonucleotide. In certain embodiments, the one or more additional linked nucleosides are at the 3' terminus of the complementary strand. In certain embodiments, the one or more additional linked nucleosides are at the 5' terminus of the complementary strand. In certain embodiments, two additional linked nucleosides are linked to a terminus. In certain embodiments, one additional nucleoside is linked to a terminus.

In certain embodiments, the compound comprises an oligonucleotide conjugated to one or more moieties which enhance the activity, cellular distribution or cellular uptake of the resulting oligonucleotides of the present invention. In certain such embodiments, the moiety is a cholesterol moiety or a lipid moiety. Additional moieties for conjugation include carbohydrates, phospholipids, biotin, phenazine, folate, phenanthridine, anthraquinone, acridine, fluoresceins, rhodamines, coumarins, and dyes. Fluorescent moieties and quenchers can be linked to the strands such that when the strands separate, the fluorescent moiety is released from the quencher and emits a detectable fluorescence. This may be useful to, for example, monitor when the miRNA is released in the target cell. In certain embodiments, a conjugate group is attached directly to an oligonucleotide. In certain embodiments, a conjugate group is attached to an oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl)cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises an oligonucleotide having one or more stabilizing groups that are attached to one or both termini of an oligonucleotide to enhance properties such as, for example, nuclease stability. Included in stabilizing groups are cap structures. These terminal modifications protect an oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Nucleobase Sequences

In certain embodiments, an oligonucleotide has a nucleobase sequence that is the same as or similar to a miRNA or a fraction thereof. Accordingly, in certain embodiments the nucleobase sequence of an oligonucleotide may have one or more mismatched basepairs with respect to, e.g., one or more of [SEQ ID NOs: 1-4] miRNA. In certain embodiments, a nucleobase sequence of an oligonucleotide of the present invention has a nucleobase sequence having one mismatch with respect to the nucleobase sequence of the mature miRNA. In certain embodiments, an oligonucleotide has a nucleobase sequence having two mismatches with respect to the nucleobase sequence of the miRNA. In certain such embodiments, an oligonucleotide has a nucleobase sequence having no more than two mismatches with respect to the nucleobase sequence of the mature miRNA. In certain such embodiments, the mismatched nucleobases are contiguous. In certain such embodiments, the mismatched nucleobases are not contiguous.

In certain embodiments, the number of linked nucleosides of an oligonucleotide is less than the length of an miRNA of the present invention. In certain such embodiments, the number of linked nucleosides of an oligonucleotide is one less than the length an miRNA of the present invention. In certain such embodiments, an oligonucleotide has one less nucleoside at the 5' terminus. In certain such embodiments, an oligonucleotide has one less nucleoside at the 3' terminus. In certain such embodiments, an oligonucleotide has two fewer nucleosides at the 5' terminus. In certain such embodiments, an oligonucleotide has two fewer nucleosides at the 3' terminus.

In certain embodiments, the number of linked nucleosides of an oligonucleotide is greater than the length an miRNA of the present invention. In certain embodiments, the number of linked nucleosides of an oligonucleotide is one greater than the length of the miRNA to which it is complementary. In certain such embodiments, the additional nucleoside is at the 5' terminus of an oligonucleotide. In certain such embodiments, the additional nucleoside is at the 3' terminus of an oligonucleotide. In certain embodiments, the number of linked nucleosides of an oligonucleotide is two greater than the length of the miRNA to which it is complementary. In certain such embodiments, the two additional nucleosides are at the 5' terminus of an oligonucleotide. In certain such embodiments, the two additional nucleosides are at the 3' terminus of an oligonucleotide. In certain such embodiments, one additional nucleoside is located at the 5' terminus and one additional nucleoside is located at the 3' terminus of an oligonucleotide.

The nucleobase sequences set forth herein, including but not limited to those found in the Exemplification and in the sequence listing, are independent of any modification to the nucleic acid. As such, nucleic acids defined by a SEQ ID NO may comprise, independently, one or more modifications to one or more sugar moieties, to one or more internucleoside linkages, and/or to one or more nucleobases.

Although the sequence listing accompanying this filing identifies each nucleobase sequence as either "RNA" or "DNA" as required, in practice, those sequences may be modified with any combination of chemical modifications. One of skill in the art will readily appreciate that such designation as "RNA" or "DNA" to describe modified oligonucleotides is somewhat arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases.

Modifications of Nucleobases

In certain embodiments, oligonucleotides provided herein may comprise one or more modifications to a nucleobase, sugar, and/or internucleoside linkage, and as such is a modified oligonucleotide. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

Thus, in certain embodiments, the modifications of the microRNA oligonucleotide strand are not only on the 5' and/or 3' terminal bases but also on the internal bases. These modifications include, but not limited to, phosphorothioated oligonucleotide, locked nucleic acid (LNA), 2' O-methyl bases, Int Desthiobiotin-TEG, 5-Methyl dC, deoxyInosine, deoxyUridine, 5-Bromo, etc, as are known by one of ordinary skill in the art.

In certain embodiments, a modified oligonucleotide comprises one or more modified nucleosides. In certain such embodiments, a modified nucleoside is a stabilizing nucleoside. An example of a stabilizing nucleoside is a sugar-modified nucleoside.

In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose.

In certain embodiments, a 2'-modified nucleoside has a bicyclic sugar moiety. In certain embodiments, the bicyclic sugar moiety is a D sugar in the alpha configuration. In certain embodiments, the bicyclic sugar moiety is a D sugar in the beta configuration. In certain embodiments, the bicyclic sugar moiety is an L sugar in the alpha configuration. In certain embodiments, the bicyclic sugar moiety is an L sugar in the beta configuration.

In certain embodiments, the bicyclic sugar moiety comprises a bridge group between the 2' and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N($R_1$)—, —C($R_1$)($R_2$)—, —C($R_1$)=C($R_1$)—, —C($R_1$)=N—, —C(=N$R_1$)—, —Si($R_1$)($R_2$)—, —S(=O)—, —C(=O)— and —C(=S)—; where each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and each substituent group is independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, amino, substituted amino, acyl, substituted acyl, $C_1$-$C_{12}$ aminoalkyl, $C_1$-$C_{12}$ aminoalkoxy, substituted $C_1$-$C_{12}$ aminoalkyl, substituted $C_1$-$C_{12}$ aminoalkoxy or a protecting group.

In some embodiments, the bicyclic sugar moiety is bridged between the 2' and 4' carbon atoms with a biradical group selected from —O—($CH_2$)$_p$—, —O—$CH_2$—, —O—$CH_2CH_2$—, —O—CH(alkyl)-, —NH—($CH_2$)$_p$—, —N(alkyl)-($CH_2$)$_p$—, —O—CH(alkyl)-, —(CH(alkyl))-($CH_2$)$_p$—, —NH—O—($CH_2$)$_p$—, —N(alkyl)-O—($CH_2$)$_p$—, or —O—N(alkyl)-($CH_2$)$_p$—, wherein p is 1, 2, 3, 4 or 5 and each alkyl group can be further substituted. In certain embodiments, p is 1, 2 or 3. In certain embodiments, a bicyclic sugar moiety is —O—($CH_2$)), also known as "locked nucleic acid" or "LNA."

In certain embodiments, a 2'-modified nucleoside comprises a 2'-substituent group selected from halo, allyl, amino, azido, SH, CN, OCN, $CF_3$, $OCF_3$, O—, S—, or N($R_m$)-alkyl; O—, S—, or N($R_m$)-alkenyl; O—, S— or N($R_m$)-alkynyl; O-alkylenyl-O-alkyl, alkynyl, alkaryl, aralkyl, O-alkaryl, O-aralkyl, O($CH_2$)$_2$$SCH_3$, O—($CH_2$)$_2$—O—N($R_m$)($R_n$) or O—$CH_2$—C(=O)—N($R_m$)($R_n$), where each $R_m$ and $R_n$ is, independently, H, an amino protecting group or substituted or unsubstituted C.sub.1-C.sub.10 alkyl. These 2'-substituent groups can be further substituted with one or more substituent groups independently selected from hydroxyl, amino, alkoxy, carboxy, benzyl, phenyl, nitro (NO.sub.2), thiol, thioalkoxy (S-alkyl), halogen, alkyl, aryl, alkenyl and alkynyl.

In certain embodiments, a 2'-modified nucleoside comprises a 2'-substituent group selected from F, $NH_2$, $N_3$, $OCF_3$, O—$CH_3$, O($CH_2$)$_3$$NH_2$, $CH_2$—CH=$CH_2$, O—$CH_2$—CH=$CH_2$, $OCH_2CH_2OCH_3$, O($CH_2$)$_2$$SCH_3$, O—($CH_2$)$_2$—O—N($R_m$)($R_n$), —O($CH_2$)$_2$—O—($CH_2$)$_2$N($CH_3$)$_2$, and N-substituted acetamide (O—CH, —C(=O)—N($R_m$)($R_n$) where each $R_m$ and $R_n$ is, independently, H, an amino protecting group or substituted or unsubstituted $C_1$-$C_{10}$ alkyl.

In certain embodiments, a 2'-modified nucleoside comprises a 2'-substituent group selected from F, $OCF_3$, O—$CH_3$, $OCH_2CH_2OCH_3$, 2'-O($CH_2$)$_2$$SCH_3$, O—($CH_2$)$_2$—O—N($CH_3$)$_2$, —O($CH_2$)$_2$O($CH_2$)$_2$N($CH_3$)$_2$, and O—$CH_2$—C(=O)—N(H)$CH_3$.

In certain embodiments, a 2'-modified nucleoside comprises a 2'-substituent group selected from F, O—$CH_3$, and $OCH_2CH_2OCH_3$.

In certain embodiments, a sugar-modified nucleoside is a 4'-thio modified nucleoside. In certain embodiments, a sugar-modified nucleoside is a 4'-thio-2'-modified nucleoside. A 4'-thio modified nucleoside has a .beta.-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include 2'-$OCH_3$, 2'-O—($CH_2$)$_2$—$OCH_3$, and 2'-F.

In certain embodiments, a modified oligonucleotide comprises one or more internucleoside modifications. In certain such embodiments, each internucleoside linkage of an oligonucleotide is a modified internucleoside linkage. In certain embodiments, a modified internucleoside linkage comprises a phosphorus atom.

In certain embodiments, a modified oligonucleotide comprises at least one phosphorothioate internucleoside linkage. In certain embodiments, each internucleoside linkage of a modified oligonucleotide is a phosphorothioate internucleoside linkage.

In certain embodiments, a modified internucleoside linkage does not comprise a phosphorus atom. In certain such embodiments, an internucleoside linkage is formed by a short chain alkyl internucleoside linkage. In certain such embodiments, an internucleoside linkage is formed by a cycloalkyl internucleoside linkages. In certain such embodiments, an internucleoside linkage is formed by a mixed heteroatom and alkyl internucleoside linkage. In certain such embodiments, an internucleoside linkage is formed by a mixed heteroatom and cycloalkyl internucleoside linkages. In certain such embodiments, an internucleoside linkage is formed by one or more short chain heteroatomic internucleoside linkages. In certain such embodiments, an internucleoside linkage is formed by one or more heterocyclic internucleoside linkages. In certain such embodiments, an internucleoside linkage has an amide backbone. In certain such embodiments, an internucleoside linkage has mixed N, O, S and CH, component parts.

In certain embodiments, a modified oligonucleotide comprises one or more modified nucleobases. In certain embodiments, a modified oligonucleotide comprises one or more 5-methylcytosines. In certain embodiments, each cytosine of a modified oligonucleotide comprises a 5-methylcytosine.

In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone. In certain embodiments, a modified nucleobase is selected from 5-substituted pyrimidines, 6-azapyrimidines and N-2, N-6 and O-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

Oligonucleotide Motifs

Suitable motifs for modified oligonucleotides of the present invention include, but are not limited to, fully modified, uniformly modified, positionally modified, and gapmer. Modified oligonucleotides having a fully modified motif, including a uniformly modified motif, may be designed to target mature miRNAs. Alternatively, modified oligonucleotides having a fully modified motif, including a uniformly modified motif, may be designed to target certain sites of pri-miRNAs or pre-miRNAs, to block the processing of miRNA precursors into mature miRNAs. Modified oligonucleotides having a fully modified motif or uniformly modified motif are effective inhibitors of miRNA activity.

In certain embodiments, a fully modified oligonucleotide comprises a sugar modification at each nucleoside. In certain such embodiments, pluralities of nucleosides are 2'-O-methoxyethyl nucleosides and the remaining nucleosides are 2'-fluoro nucleosides. In certain such embodiments, each of a plurality of nucleosides is a 2'-O-methoxyethyl nucleoside and each of a plurality of nucleosides is a bicyclic nucleoside. In certain such embodiments, a fully modified oligonucleotide further comprises at least one modified internucleoside linkage. In certain such embodiments, each internucleoside linkage of a fully sugar-modified oligonucleotide is a modified internucleoside linkage. In certain embodiments, a fully sugar-modified oligonucleotide further comprises at least one phosphorothioate internucleoside linkage. In certain such embodiments, each internucleoside linkage of a fully sugar-modified oligonucleotide is a phosphorothioate internucleoside linkage.

In certain embodiments, a fully modified oligonucleotide is modified at each internucleoside linkage. In certain such embodiments, each internucleoside linkage of a fully modified oligonucleotide is a phosphorothioate internucleoside linkage.

In certain embodiments, a uniformly modified oligonucleotide comprises the same sugar modification at each nucleoside. In certain such embodiments, each nucleoside of a modified oligonucleotide comprises a 2'-O-methoxyethyl sugar modification. In certain embodiments, each nucleoside of a modified oligonucleotide comprises a 2'-O-methyl sugar modification. In certain embodiments, each nucleoside of a modified oligonucleotide comprises a 2'-fluoro sugar modification. In certain such embodiments, a uniformly modified oligonucleotide further comprises at least one modified internucleoside linkage. In certain such embodiments, each internucleoside linkage of a uniformly sugar-modified oligonucleotide is a modified internucleoside linkage. In certain embodiments, a uniformly sugar-modified oligonucleotide further comprises at least one phosphorothioate internucleoside linkage. In certain such embodiments, each internucleoside linkage of a uniformly sugar-modified oligonucleotide is a phosphorothioate internucleoside linkage.

In certain embodiments, a uniformly modified oligonucleoside comprises the same internucleoside linkage modifications throughout. In certain such embodiments, each internucleoside linkage of a uniformly modified oligonucleotide is a phosphorothioate internucleoside linkage.

In certain embodiments, a positionally modified oligonucleotide comprises regions of linked nucleosides, where each nucleoside of each region comprises the same sugar moiety, and where each nucleoside of each region comprises a sugar moiety different from that of an adjacent region.

In certain embodiments, a positionally modified oligonucleotide(s) as taught and exemplified in US Patent Publication No. 2012/0122959, which is incorporated herein by reference. comprises at least 10 2'-fluoro modified nucleosides. Additional motifs beyond those taught in US 2012/0122959 are disclosed in PCT Publication No. WO/2007/112754, which is herein incorporated by reference in its entirety for the description of oligonucleotide modifications and patterns of oligonucleotide modifications.

A modified oligonucleotide having a gapmer motif may have an internal region consisting of linked 2'-deoxynucleotides, and external regions consisting of linked 2'-modified nucleosides. Such a gapmer may be designed to elicit RNase H cleavage of a miRNA precursor. The internal 2'-deoxynucleoside region serves as a substrate for RNase H, allowing the cleavage of the miRNA precursor to which a modified oligonucleotide is targeted. In certain embodiments, each nucleoside of each external region comprises the same 2'-modified nucleoside. In certain embodiments, one external region is uniformly comprised of a first 2'-modified nucleoside and the other external region is uniformly comprised of a second 2'-modified nucleoside.

A modified oligonucleotide having a gapmer motif may have a sugar modification at each nucleoside. In certain embodiments, the internal region is uniformly comprised of a first 2'-modified nucleoside and each of the external regions is uniformly comprised of a second 2'-modified nucleoside. In certain such embodiments, the internal region is uniformly comprised of 2'-fluoro nucleosides and each external region is uniformly comprised of 2'-O-methoxyethyl nucleosides.

In certain embodiments, each external region of a gapmer consists of linked 2'-O-methoxyethyl nucleosides. In certain embodiments, each external region of a gapmer consists of linked 2'-O-methyl nucleosides. In certain embodiments, each external region of a gapmer consists of 2'-fluoro nucleosides. In certain embodiments, each external region of a gapmer consists of linked bicyclic nucleosides.

In certain embodiments, each nucleoside of one external region of a gapmer comprises 2'-O-methoxyethyl nucleosides and each nucleoside of the other external region comprises a different 2'-modification. In certain such embodiments, each nucleoside of one external region of a gapmer comprises 2% O-methoxyethyl nucleosides and each nucleoside of the other external region comprises 2'-O-methyl nucleosides. In certain such embodiments, each nucleoside of one external region of a gapmer comprises 2'-O-methoxyethyl nucleosides and each nucleoside of the other external region comprises 2'-fluoro nucleosides. In certain such embodiments, each nucleoside of one external region of a gapmer comprises 2'-O-methyl nucleosides and each nucleoside of the other external region comprises 2'-fluoro nucleosides. In certain such embodiments, each nucleoside of one external region of a gapmer comprises 2'-O-methoxyethyl nucleosides and each nucleoside of the other external region comprises bicyclic nucleosides. In certain such embodiments, each nucleoside of one external region of a gapmer comprises 2'-O-methyl nucleosides and each nucleoside of the other external region comprises bicyclic nucleosides.

In certain embodiments, nucleosides of one external region comprise two or more sugar modifications. In certain embodiments, nucleosides of each external region comprise two or more sugar modifications. In certain embodiments, at least one nucleoside of an external region comprises a 2'-O-methoxyethyl sugar and at least one nucleoside of the same external region comprises a 2'-fluoro sugar. In certain embodiments, at least one nucleoside of an external region comprises a 2'-O-methoxyethyl sugar and at least one nucleoside of the same external region comprises a bicyclic sugar moiety. In certain embodiments, at least one nucleoside of an external region comprises a 2'-O-methyl sugar and at least one nucleoside of the same external region comprises a bicyclic sugar moiety. In certain embodiments at least one nucleoside of an external region comprises a 2'-O-methyl sugar and at least one nucleoside of the same external region comprises a 2'-fluoro sugar. In certain embodiments, at least one nucleoside of an external region comprises a 2'-fluoro sugar and at least one nucleoside of the same external region comprises a bicyclic sugar moiety.

In certain embodiments, each external region of a gapmer consists of the same number of linked nucleosides. In certain embodiments, one external region of a gapmer consists a number of linked nucleosides different than that of the other external region.

Additional Therapies

Treatments for obesity and other related metabolic disorders may comprise more than one therapy. As such, in certain embodiments the present invention provides methods for treating metabolic disorders comprising administering to a subject in need thereof a compound comprising an oligonucleotide, the oligonucleotide comprising or consisting of miRNA-455, e.g., one or more of [SEQ ID NOs: 1-4], or a functional portion or fragment thereof, and further comprising administering at least one additional pharmaceutical agent.

In certain embodiments, the additional pharmaceutical agent is a glucose-lowering agent.

In certain embodiments, the glucose-lowering agent is a PPAR agonist (gamma, dual, or pan), a dipeptidyl peptidase (IV) inhibitor, a GLP-I analog, insulin or an insulin analog, an insulin secretagogue, a SGLT2 inhibitor, a human amylin analog, a biguanide, an alpha-glucosidase inhibitor, a meglitinide, a thiazolidinedione, or a sulfonylurea.

In certain embodiments, the glucose-lowering agent is a GLP-I analog. In certain embodiments, the GLP-I analog is exendin-4 or liraglutide.

In certain embodiments, the glucose-lowering agent is a sulfonylurea. In certain embodiments, the sulfonylurea is acetohexamide, chlorpropamide, tolbutamide, tolazamide, glimepiride, a glipizide, a glyburide, or a gliclazide.

In certain embodiments, the glucose-lowering agent is a biguanide. In certain embodiments, the biguanide is metformin. In certain embodiments, blood glucose levels are decreased without increased lactic acidosis as compared to the lactic acidosis observed after treatment with metformin alone.

In certain embodiments, the glucose-lowering agent is a meglitinide. In certain embodiments, the meglitinide is nateglinide or repaglinide.

In certain embodiments, the glucose-lowering agent is a thiazolidinedione. In certain embodiments, the thiazolidinedione is pioglitazone, rosiglitazone, or troglitazone. In certain embodiments, blood glucose levels are decreased without greater weight gain than observed with rosiglitazone treatment alone.

In certain embodiments, the glucose-lowering agent is an alpha-glucosidase inhibitor. In certain embodiments, the alpha-glucosidase inhibitor is acarbose or miglitol.

In certain embodiments, the glucose-lowering agent is an antisense oligonucleotide targeted to PTP1B.

In certain embodiments, an additional therapy is an anti-obesity agent. In certain embodiments, an anti-obesity agent is Orlistat, Sibutramine, or Rimonabant.

In a certain embodiment, the additional therapy is therapeutic lifestyle change. In certain embodiments, the therapeutic lifestyle change includes an exercise regimen and/or diet.

In certain embodiments the dose of an additional pharmaceutical agent is the same as the dose that would be administered if the additional pharmaceutical agent was administered alone.

In certain embodiments the dose of an additional pharmaceutical agent is lower than the dose that would be administered if the additional pharmaceutical agent was administered alone. In certain embodiments the dose of an additional pharmaceutical agent is greater than the dose that would be administered if the additional pharmaceutical agent was administered alone.

Further examples of additional pharmaceutical agents include, but are not limited to, corticosteroids, including but not limited to prednisone; immunoglobulins, including, but not limited to intravenous immunoglobulin (IVIg); analgesics (e.g., acetaminophen); anti-inflammatory agents, including, but not limited to non-steroidal anti-inflammatory drugs (e.g., ibuprofen, COX-I inhibitors, and COX-2, inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

In certain embodiments, an additional therapy is a lipid-lowering therapy. In certain such embodiments, a lipid-lowering therapy is therapeutic lifestyle change. In certain such embodiments, a lipid-lowering therapy is LDL apheresis.

Pharmaceutical Compositions

Provided herein are pharmaceutical compositions comprising oligonucleotides. In certain embodiments, such pharmaceutical compositions are used for the treatment of metabolic disorders such as obesity and associated conditions. In certain embodiments, a pharmaceutical composition provided herein comprises a compound comprising or consisting of an oligonucleotide sequence of the present invention, or functional fragment or modified version thereof, such as, for example, one or more of [SEQ ID NOs: 1-4].

Suitable administration routes include, but are not limited to, oral, rectal, transmucosal, intestinal, enteral, topical, suppository, through inhalation, intrathecal, intraventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into adipose tissue).

In certain embodiments, a pharmaceutical composition is administered in the form of a dosage unit (e.g., tablet, capsule, bolus, etc.). In certain embodiments, such pharmaceutical compositions comprise an oligonucleotide in a dose selected from approximately 1 µg up to 1 mg, 1 mg up to 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 ma, 495 mg, 500 mg, 505 mg, 510 mg, 515 mg, 520 ma, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg and intermittent values. In certain such embodiments, a pharmaceutical composition of the comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical agent is sterile lyophilized modified oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of an oligonucleotide which has been prepared in water for injection, or in saline for injection, adjusted to pH 7.0-9.0 with acid or base during preparation, and then lyophilized. The lyophilized modified oligonucleotide may be from approximately 1 mg up to 25-800 mg of an oligonucleotide. It is understood that this encompasses 1, 5, 10, 15, 20, 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide, and intermittent values. The lyophilized drug product may be packaged in a 2 mL Type I, clear glass vial (ammonium sulfate-treated), stoppered with a bromobutyl rubber closure and sealed with an aluminum FLIP-OFF™ overseal.

In certain embodiments, the pharmaceutical compositions provided herein may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

Lipid moieties have been used in nucleic acid therapies in a variety of methods. In one method, the nucleic acid is introduced into preformed liposomes or lipoplexes made of mixtures of cationic lipids and neutral lipids. In another method, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, INTRALIPID™ is used to prepare a pharmaceutical composition comprising an oligonucleotide. Intralipid is fat emulsion prepared for intravenous administration. It is made up of 10% soybean oil, 1.2% egg yolk phospholipids, 2.25% glycerin, and water for injection. In addition, sodium hydroxide has been added to adjust the pH so that the final product pH range is 6 to 8.9.

In certain embodiments, a pharmaceutical composition provided herein comprise a polyamine compound or a lipid moiety complexed with a nucleic acid, as is known to one of ordinary skill in the art. Such preparations are described in PCT publication WO/2008/042973, which is herein incorporated by reference in its entirety for the disclosure of lipid preparations. Certain additional preparations are described in Akinc, et al., Nature Biotechnology 26, 561-569 (1 May 2008), which is herein incorporated by reference in its entirety for the disclosure of lipid preparations, as are known to one of ordinary skill in the art.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein is prepared using known techniques, including, but not limited to mixing, dissolving, granulating, dragee-making, levigating, emulsifying, encapsulating, entrapping or tabletting processes.

In certain embodiments, a pharmaceutical composition provided herein is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition provided herein is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition provided herein is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide (DMSO) are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition provided herein is prepared for oral administration. In certain of such embodiments, a pharmaceutical composition is formulated by combining one or more compounds comprising an oligonucleotide with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotides provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Kits

The present invention also provides kits. In some embodiments, the kits comprise one or more compounds of the invention comprising a modified oligonucleotide, wherein the nucleobase sequence of the oligonucleotide is miRNA-455, e.g., one or more of [SEQ ID NOs: 1-4] or a composition comprising miRNA-455. The composition may be present within a vial or other suitable receptacle. A plurality of vials or receptacles, such as 10, can be present in, for example, dispensing packs. In some embodiments, the vial is manufactured so as to be accessible with a syringe. The kit can also contain instructions for using the compounds of the present invention. In some embodiments, the kits may be used for administration of the compounds of the present invention to a subject.

Experimental Models

In certain embodiments, the present invention provides methods of using and/or testing modified oligonucleotides of the present invention in an experimental model. Those having skill in the art are able to select and modify the protocols for such experimental models to evaluate a pharmaceutical agent of the invention.

Generally, the oligonucleotides of the present invention (and modified oligonucleotides) are first tested in cultured cells. Suitable cell types include those that are related to the cell type to which delivery of an oligonucleotide is desired in vivo. For example, suitable cell types for the study of the methods described herein include primary adipocytes (BAT and WAT), preadipocytes, differentiated adipocytes, HepG2 cells, Huh7 cells, 3T3L1 cells, and C2C12 cells (murine myoblasts).

In certain embodiments, the extent to which an oligonucleotide activates, augments or interferes with the activity of a miRNA is assessed in cultured cells. In certain embodiments, augmentation of inhibition of miRNA activity may be assessed by measuring the levels of the miRNA. Alternatively, the level of a predicted or validated miRNA target may be measured. An augmentation or inhibition of miRNA activity may result in the increase in the mRNA and/or protein of a miRNA target. Further, in certain embodiments, certain phenotypic outcomes may be measured. For example, suitable phenotypic outcomes include increases in BAT cell number or cell activity and/or modulation of specific signal pathway components, as detailed in the Exemplification section below.

Suitable experimental animal models for the testing of the methods described herein include: ob/ob mice (a model for diabetes, obesity and insulin resistance), db/db mice (a model for diabetes, obesity and insulin resistance), high-fat fed C57B16/J mice, nude mice, Zucker diabetic rats, and transgenic mice, examples of which are given herein.

Quantitation Assays

The effects of augmentation or inhibition of a miRNA following the administration of the oligonucleotides of the present invention (or modified oligonucleotides) may be assessed by a variety of methods known in the art. In certain embodiments, these methods are be used to quantitate miRNA levels in cells or tissues in vitro or in vivo. In certain embodiments, changes in miRNA levels are measured by microarray analysis. In certain embodiments, changes in miRNA levels are measured by one of several commercially available PCR assays, such as the TaqMan™ MicroRNA Assay (Applied Biosystems). In certain embodiments, antisense inhibition of a miRNA is assessed by measuring the mRNA and/or protein level of a target of a miRNA. Modulation of an miRNA generally results in the increase in the level of mRNA and/or protein of a target of the miRNA.

The following examples are presented in order to more fully illustrate some embodiments of the invention. They should, in no way be construed, however, as limiting the broad scope of the invention.

EXEMPLIFICATION

Increasing evidence has demonstrated that miRNAs, a class of short non-coding RNAs, represent a new layer of fundamental regulatory mechanism of gene expression in addition to transcriptional and translational regulation (Almeida, et al., (2011) Mutat. Res. 717(1-2):1-8), and are important regulators of diverse biological processes such as development, disease and establishment of cell identity. (Montano (2011) Transl. Res. 157(4):157). It has been reported that TGF-β/BMP signaling pathway regulates miRNA expression and maturation (A. Hata and B. N. Davis, "Control of microRNA biogenesis by TGFbeta signaling pathway-A novel role of Smads in the nucleus," Cytokine Growth Factor Rev. 20(5-6), 517 (2009)), and that miRNAs could regulate white adipogenesis (K. Kajimoto, H. Naraba, and N. Iwai, "MicroRNA and 3T3-L1 preadipocyte differentiation," RNA. 12(9), 1626 (2006); S. Y. Kim, et al., "miR-27a is a negative regulator of adipocyte differentiation via suppressing PPARgamma expression," Biochem. Biophys. Res. Commun. 392(3), 323 (2010)) and cell fate decision (M. Mann, et al., "miRNA-based mechanism for the commitment of multipotent progenitors to a single cellular fate," Proc. Natl. Acad. Sci. U.S.A. 107(36), 15804 (2010)). Recently, it was reported that miR-193b-365 (L. Sun, "Mir193b-365 is essential for brown fat differentiation," (2011)), miR-196a (M. Mori, et al., "Essential role for miR-196a in brown adipogenesis of white fat progenitor cells," PLoS. Biol. 10(4), e1001314 (2012)) and miR-133 (M. Trajkovski, et al., "MyomiR-133 regulates brown fat differentiation through Prdm16," Nat. Cell Biol. 14(12), 1330 (2012); H. Yin, et al., "MicroRNA-133 Controls Brown Adipose Determination in Skeletal Muscle Satellite Cells by Targeting Prdm16," Cell Metab 17(2), 210 (2013)) are involved in brown adipogenesis.

However, it remains elusive for a precise mechanism in which miRNAs modulate key signaling pathways leading to mitochondria biogenesis and UCP1 expression, the defining signature of brown adipogenesis. Further, miRNAs that modulate BAT physiology likely induce their effects via very different molecular pathways, making the discovery of any one miRNA of little, if any, help than the discovery of any other BAT inducing miRNA. This is in fact the case in that the present invention utilizes a new and non-obvious miRNA wherein up-regulation of the miRNA effects the activation and differentiation of BAT via the downregulation of key inhibitors of BAT differentiation, as compared to other systems wherein the down-regulation of the miRNA promotes the desired changes in physiology by preventing or reducing concomitant inhibition.

Using miRNA array coupled with bioinformatics analysis by program mirBridge (J. S. Tsang, "Genome-wide dissection of microRNA functions and cotargeting networks using gene set signatures," (2010)), here it is shown that the novel and non-obvious miR-455 induced brown adipogenesis of committed preadipocytes and non-committed progenitor cells by inducing PGC1α expression and mitochondria biogenesis. The exemplification demonstrates that miR-455 targets on several key adipogenic regulators including necdin, Runx1t1, and HIF1an. Necdin and Rux1t1 are major adipogenic suppressors gating adipocyte differentiation program, while HIF1an is a hydroxylase which modifies the AMPKα1 by hydroxylation. We showed that HIF1an interacts with AMPKα1 and inhibits its activity. Thus, it is provided herein that miR-455 suppresses necdin and Runx1t1 to initiate the general adipogenic program, and suppresses HIF1an to activate AMPKα1 which in turn acts as metabolic trigger to induce the browning program including PGC1α, mitochondria biogenesis and UCP1 expression.

Although the present invention is not limited by how it works, it is believed that miRNAs regulate gene expression by targeting mRNA 3'UTR (untranslated region), leading to translational repression and/or mRNA degradation. It remains a challenging issue to those of ordinary skill in the art to identify miRNA targets involved in a specific signaling in that miRNA can have hundreds of potential targets. The common strategy of miRNA array identifies miRNAs in a given experimental setting, but lacks signaling guidance. Dr. John Tsang and colleagues developed the computational program mirBridge for identifying miRNAs that may regulate a specific signaling pathway based on gene set enrichment analysis (J. S. Tsang, "Genome-wide dissection of microRNA functions and cotargeting networks using gene set signatures," (2010)). From evolutionary point of view, if a set of miRNAs are involved in a specific signaling pathway, it is likely that the target sites of these miRNAs are enriched in the 3'UTRs of the genes regulating the same signaling pathway. Thus, by starting with a gene set of known function, mirBridge can assess whether the functional sites (usually seed region) for a given miRNA are enriched in the gene set, and therefore identify the enriched miRNAs. This will lead to the possibility that one miRNA targets multiple components of a signaling pathway and a set of miRNAs may co-target a signaling network. We designed strategy combining classic miRNA array and mirBridge analysis (FIG. 1a). First, we performed classic miRNA array on C3H10T1/2 cells treated with BMP7 vs. vehicle to obtain miRNAs regulated by BMP7. Second, we performed microarray analysis and obtained gene sets from 3 sets of cellular models: 1) multipotent progenitor C3H10T1/2 cells treated with BMP7 vs. vehicle; 2) Muscle Sca-1+ Progenitor Cells (ScaPCs) (T. J. Schulz, "Identification of inducible brown adipocyte progenitors residing in skeletal muscle and white fat," (2011)) from C57BL/6 mice treated BMP7 vs. vehicle; and 3) Muscle ScaPCs from 129-S1 mice vs. C57BL/6 mice. Then we subjected the 3 gene sets to mirBridge analysis to obtain 3 sets of miRNAs whose target sites are enriched in the genes involved in signaling pathways regulated by BMP7. C3H10T1/2 cells were able to commit to brown adipogenic lineage upon BMP7 pretreatment (Y. H. Tseng, et al., "New role of bone morphogenetic protein 7 in brown adipogenesis and energy expenditure," Nature 454(7207), 1000 (2008)). Muscle ScaPCs (T. J. Schulz, "Identification of inducible brown adipocyte progenitors residing in skeletal muscle and white fat," (2011)) represent an inducible brown fat progenitors. And, ScaPCs from obesity-resistant 129-S1 mice exhibited markedly higher thermogenic capacity than those isolated from obesity-prone C57BL/6 mice (T. J. Schultz, ibid.). Thus, the genes identified from the three sets of microarrays represent those involved in regulating brown adipogenic commitment and differentiation, as well as regulating thermogenic capacity; and the miRNAs identified by mirBridge defines those involved in brown adipogenic and thermogenic regulation. The miRNAs significantly regulated by BMP7 in miRNA array and among the top 20 of at least 2 of the 3 sets in mirBridge analysis are selected (FIG. 6).

With these mRNA candidates, their tissue specificities were examined using Q-RT-PCR, and only miR-455-3p (miR-455 hereafter) showed BAT specific expression (FIG. 1b). miR-455 expression was upregulated during BMP7-induced brown adipocyte differentiation of both C3H10T/1/2 cells (FIG. 1c) and brown preadipocytes (FIG. 1d). Importantly, miR-455 expression in the interscapular BAT was induced upon short-term cold exposure, suggesting its function in mediating β-adrenergic stimulation of thermogenesis (FIG. 1e).

Figure 2B:
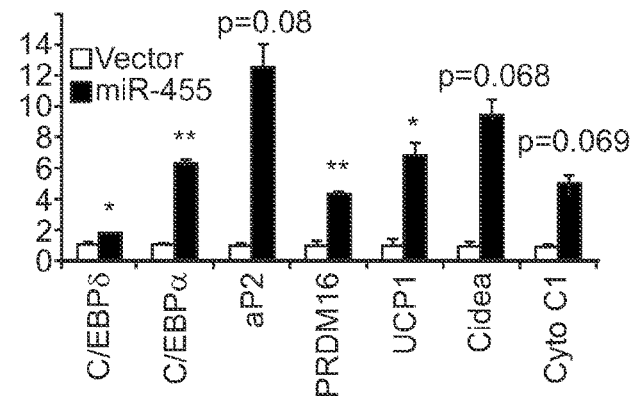
Figure 2C:
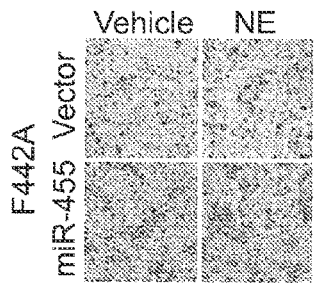
Figure 2D:
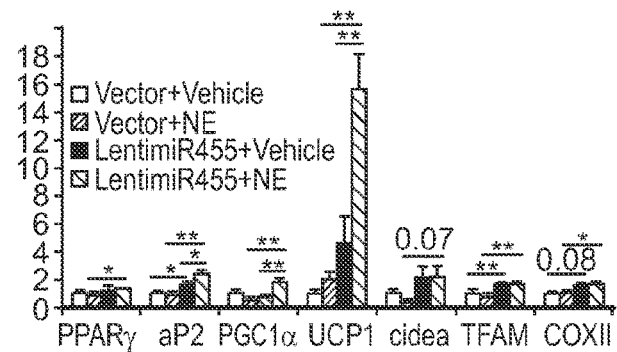
Figure 2E:
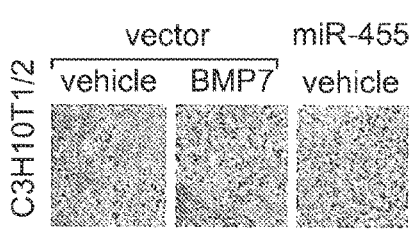
Figure 2F:
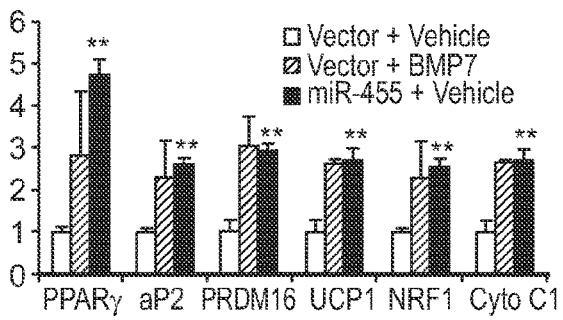

To address the function of miR-455, miR-455 was overexpressed in three different cellular models: brown preadipocytes, white preadipocyte 3T3-F442A and multipotent progenitor cell C3H10T1/2. Lentiviral delivery achieved 16-40 fold overexpression of miR-455 in the 3 cell models (FIG. 2a, 2d, 2g, 7a). Overexpression of miR-455 in brown preadipocytes induced the cells to differentiate into mature brown adipocytes when incubated with cocktail containing only insulin and $T_3$ but without the classic adipogenic inducers (Dex and IBMX) for 17 days, as evidenced by both lipid accumulation (FIG. 2b) and increased expression of adipogenic and brown fat-defining genes (FIG. 2c). This indicated that miR-455 to a significant extent could substitute for the adipogenic inducers in this setting. While overexpression of miR-455 alone in 3T3-F442A cells only mildly enhanced differentiation (FIG. 2e), simultaneous treatment with Norepinephrine (NE) markedly induced brown adipogenesis of the cells as evidenced by significantly increased UCP1 and PGC1α expression (FIG. 2d). It was previously shown by our lab that BMP7 pretreatment followed standard adipogenic induction induced brown adipocyte differentiation of C3H10T1/2 cells (Y. H. Tseng, et al., "New role of bone morphogenetic protein 7 in brown adipogenesis and energy expenditure," Nature 454(7207), 1000 (2008)). When subjected to standard adipogenic induction, miR-455-overexpressing C3H10T1/2 cells were able to differentiate into mature brown adipocytes (FIG. 2e) expressing UCP1, PRDM16 and mitochondrial genes at the level comparable to that of BMP7 pretreatment (FIG. 2f), suggesting that miR-455 could partially mediate the effect of BMP7 on the commitment of the multipotent progenitor cells along brown adipogenic lineage. These data demonstrated that miR-455 was able to induce both the brown adipogenic commitment and differentiation of various cell models in vitro.

Figure 3A:
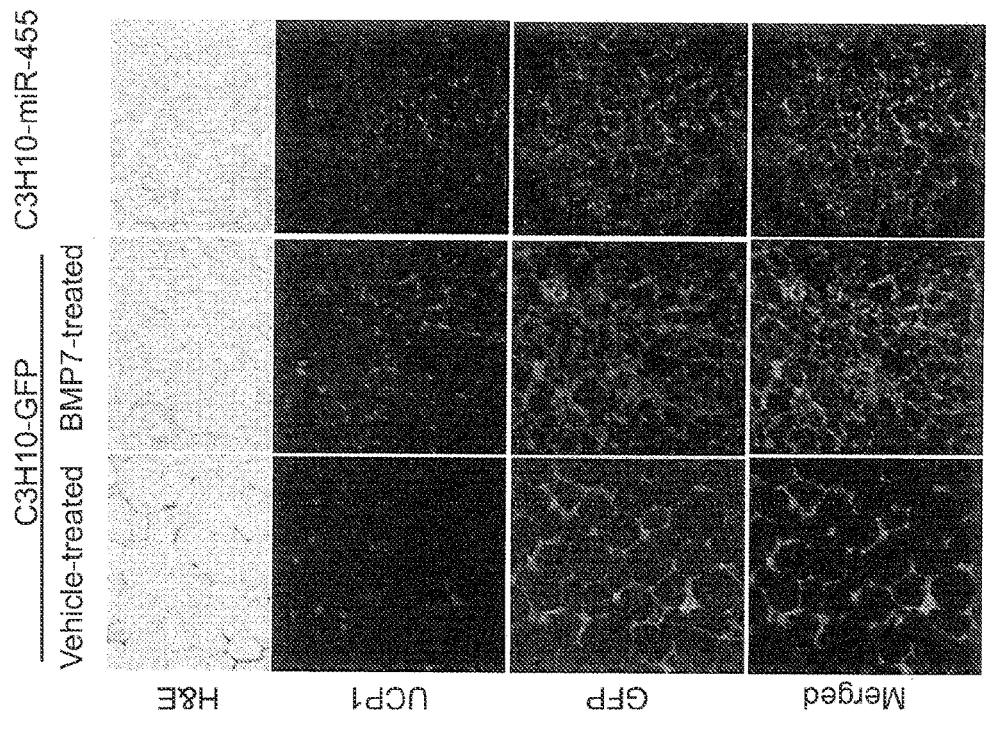
FIG. 3 shows miR-455 overexpression induced UCP1 expression in vivo. a, b, C3H10T1/2-GFP and -lentimiR-455 cells were injected into the thoracic area of male nude mice subcutaneously. Implanted cells were dissected for histology and analyzed by H&E staining and immunostaining (a); nude mice implanted were analyzed by CLAMS (b). (n=6) c, aP2-miR-455 transgenic mice were created on C57BL/6 background. miR-455 and gene expression were quantified by Q-RT-PCR. (n=3-8) (* p<0.05,  p<0.01, * p<0.001, ** p<0.0001, **** p<0.000001).
Figure 3B:
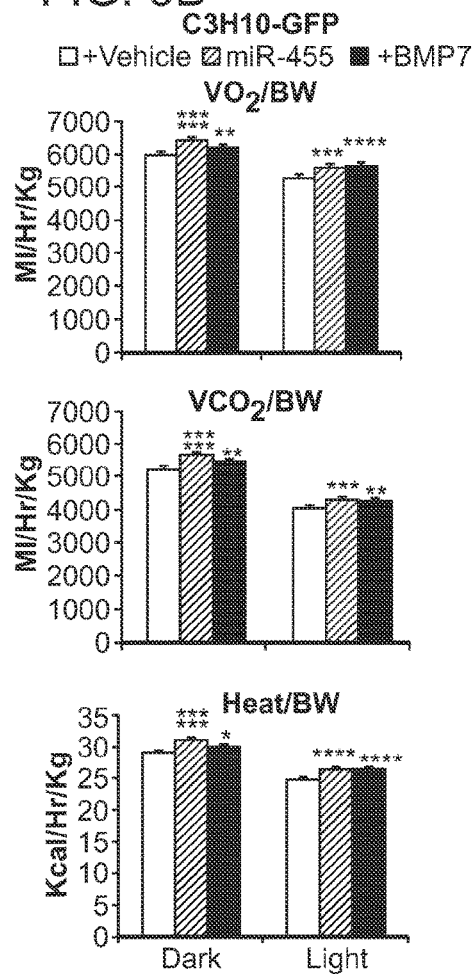
Figure 3C:
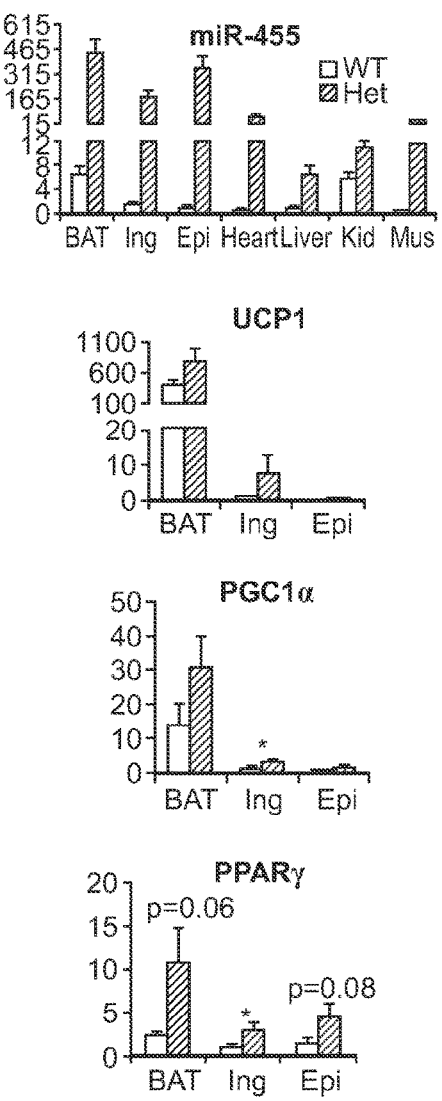
Figure 10:
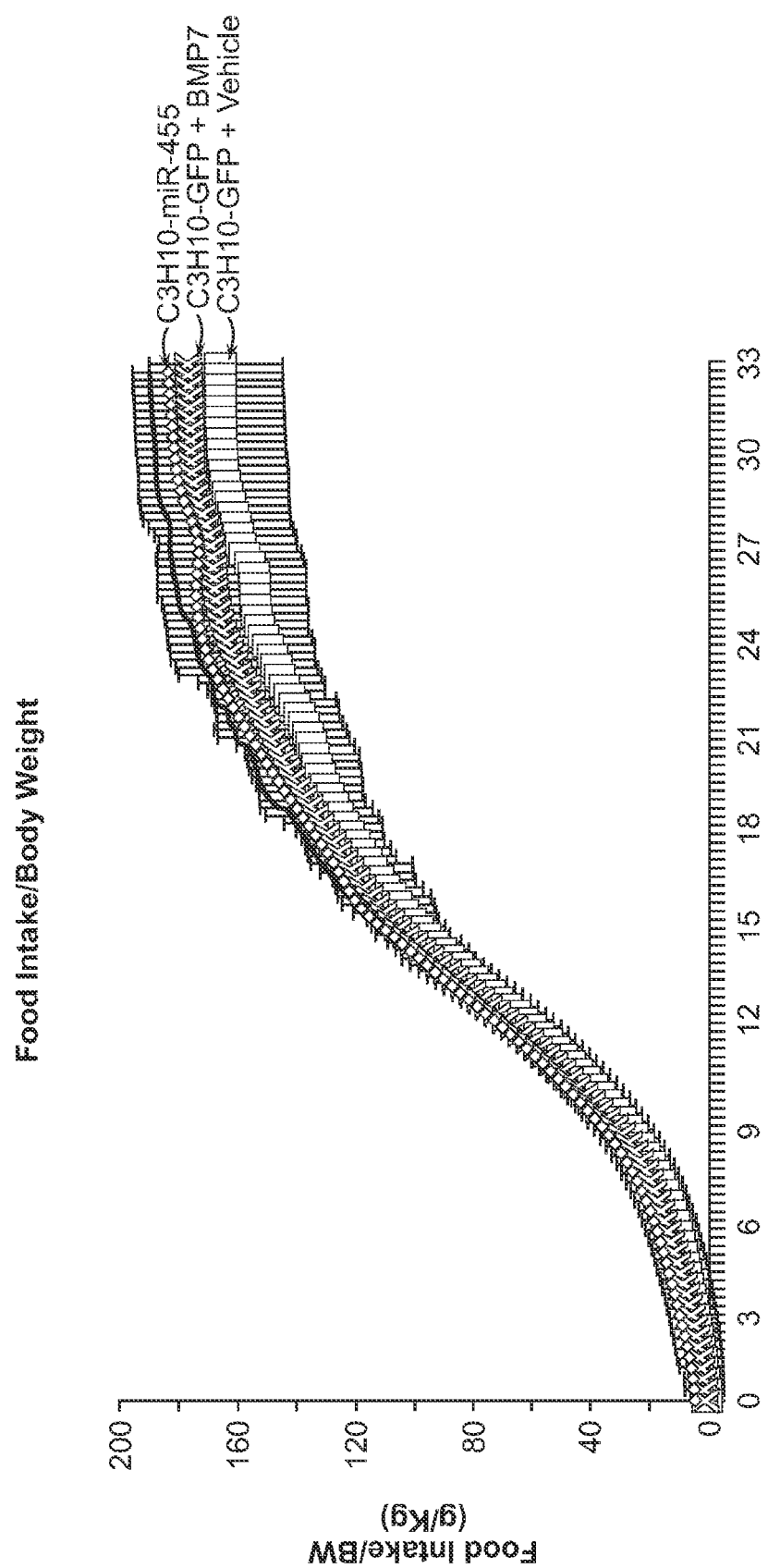
FIG. 10 shows food intake during CLAMS from mice injected with C3H10T1/2 cells pretreated with vehicle or BMP7, or overexpressing miR-455 as FIG. 3a, 3b.
Figure 17A:
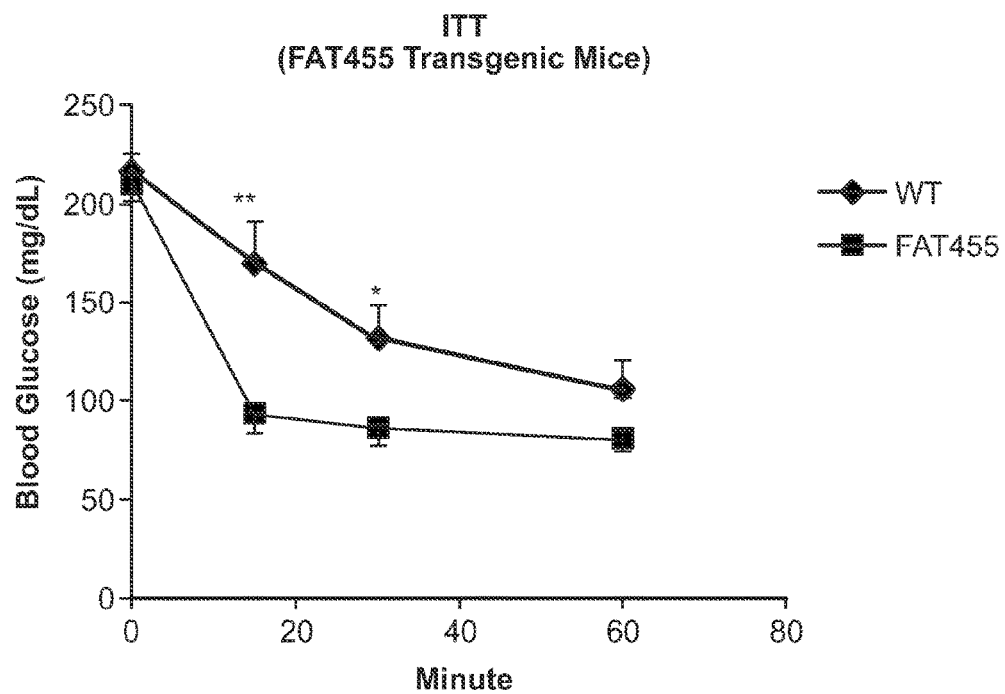
FIG. 17 shows Blood Glucose levels of aP2-mi455 transgenic mice vs. wild type (WT). aP2-miR455 (FAT455) transgenic mice (C57BL/6 background) at age of 8-9 weeks maintained at room temperature were subjected to standard IP-ITT and IP-GTT tests.
Figure 17B:
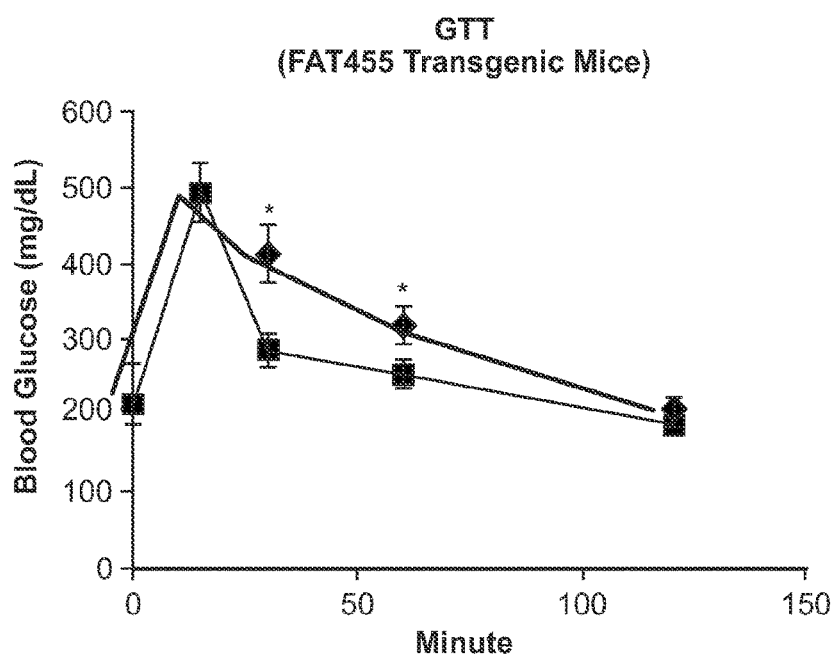

Next, whether miR-455 could induce brown adipogenesis in vivo was examined. First, C3H10T1/2-miR455, and C3H10T1/2-GFP (control, treated with vehicle or BMP7) cells were implanted subcutaneously into the thoracic region of athymic nude mice. Five weeks after implantation, both vehicle-treated C3H10T1/2-miR455 cells and BMP7-treated C3H10T1/2-GFP control cells developed into multilocular UCP1-positive brown adipocytes (FIG. 3a), while vehicle-treated C3H10T1/2-GFP cells developed into unilocular UCP1-negative white adipocytes (FIG. 3a). This result verified our in vitro observation that miR-455 was able to induce brown adipogenic commitment and differentiation of multipotent progenitor cells. When the implanted mice were subjected to CLAMS analysis, C3H10T1/2-miR455-injected and C3H10T1/2-GFP-BMP7-injected mice exhibited significantly higher oxygen consumption, higher $CO_2$ production and higher heat generation than the control C3H10T1/2-GFP-vehicle-injected mice (FIG. 3b), showing that miR-455 was able to enhance thermogenesis-mediated energy expenditure through inducing UCP1 expression in vivo. Second, transgenic mice expressing miR-455 specifically in adipose tissue using aP2 promoter were generated. Tissue expression examination by Q-RT-PCR confirmed that the aP2-miR455 transgenic heterogenetic mice (Het) achieved 60-400 folder overexpression of miR-455 in adipose tissues including interscapular brown tissue (BAT) and inguinal (Ing) and epidydimal (Epi) white adipose tissue (WAT), although up to 20 fold overexpression was also observed in heart, muscle and liver and kidney (FIG. 3c). Q-RT-PCR revealed that the transgenic Het mice showed mild but significantly elevated expression of UCP1, PGC1α and PPARγ2 (FIG. 3c). Food intake for these mice is shown in FIG. 10. Glucose tolerance curves are shown in FIG. 17.

Figure 11C:
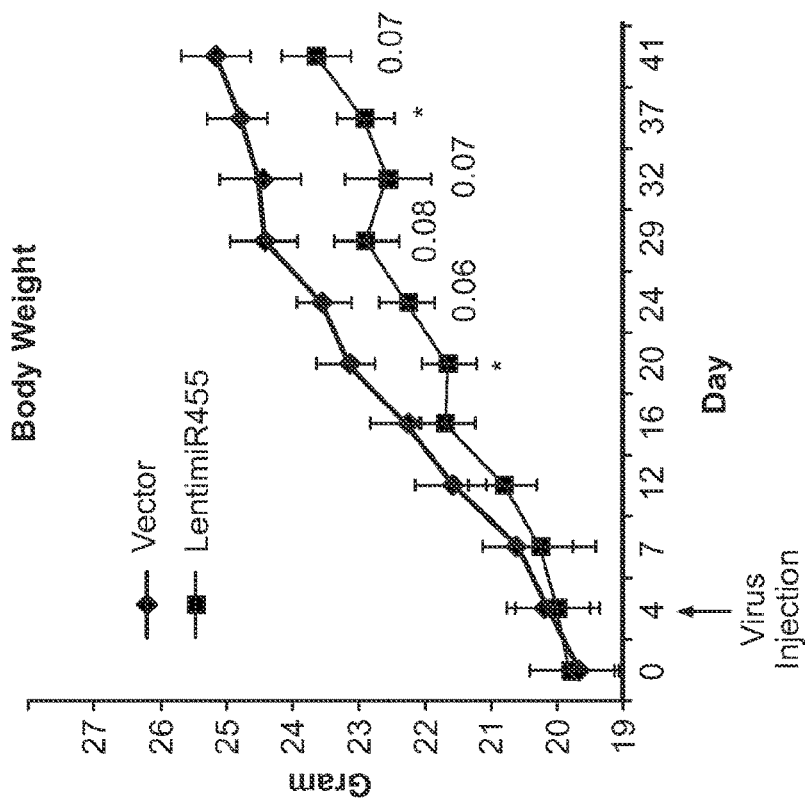
FIG. 11 shows the interscapular brown fat depot (iBAT) of C57B/L6 mice were exposed by small Incision, and LentimiR-455 lentivirus were injected directly into the iBAT. Five weeks after Injection, CLAMS was performed. Six weeks after injection, mice were sacrificed, tissues isolated and analyzed for gene expression. a, miR-455 expression in iBAT. b, UCP1 expression in iBAT. c, mice were maintained in standard chow diet for 6 weeks, body weight were measured every $4^{th}$ or $5^{th}$ day. Star asterisk or p values were placed along the curve. d, Insulin Tolerance Test. e, Glucose Tolerance Test. (*p<0.05, **p<0.01, n=6).
Figure 11A:
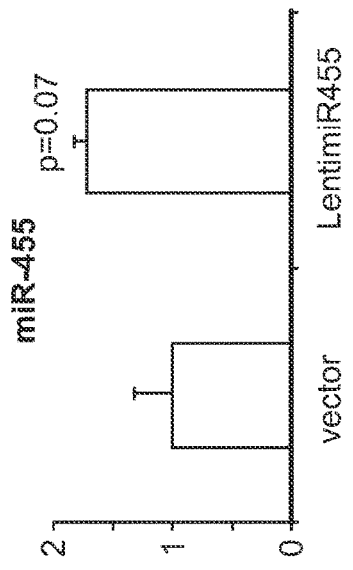
Figure 11B:
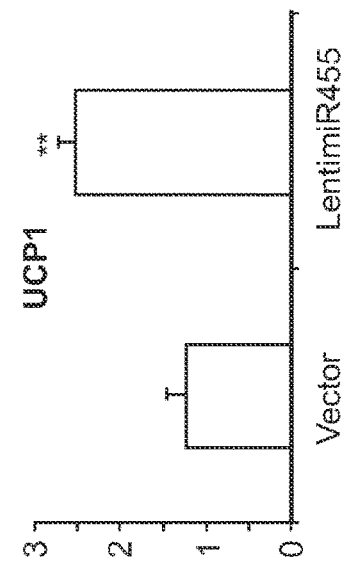
Figure 11D:
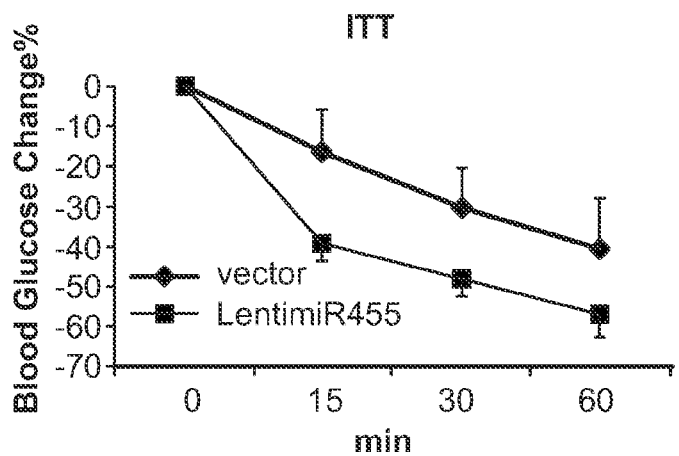
Figure 11E:
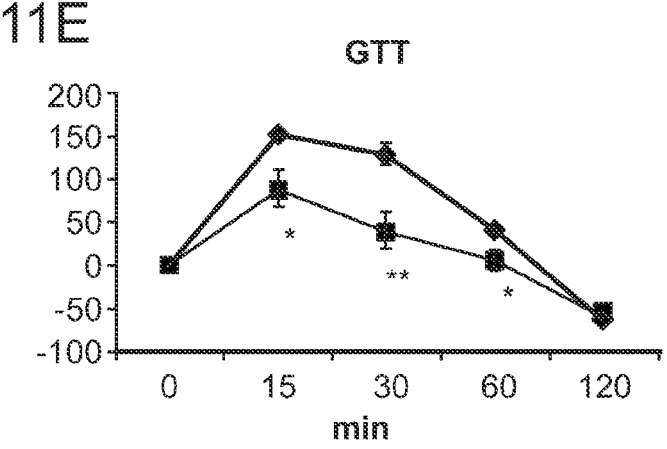

Third, miR-455 lentivirus were injected directly into interscapular BAT of C57BL/6 mice through surgical procedure. LentimiR-455 virus injection achieved 70% higher miR-455 expression over control virus injection (FIG. 11a). Importantly, BAT from LentimiR-455-injected mice expressed 2 fold higher UCP1 than control virus-injected mice (FIG. 11b). Consistently, lentimiR-455-injected mice had lower body weight compared to control virus injected mice (FIG. 11c), improved insulin tolerance (FIG. 11d), and improved glucose tolerance (FIG. 11e).

Figure 2H:
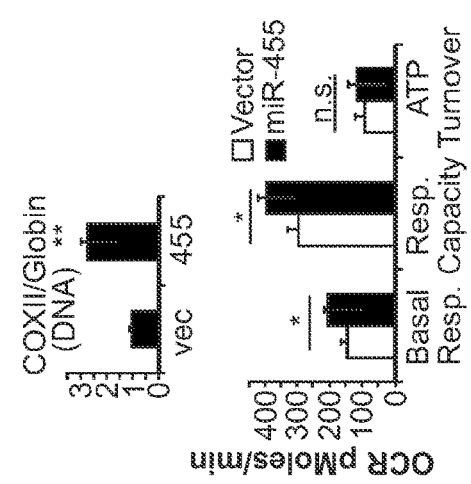
Figure 2I:
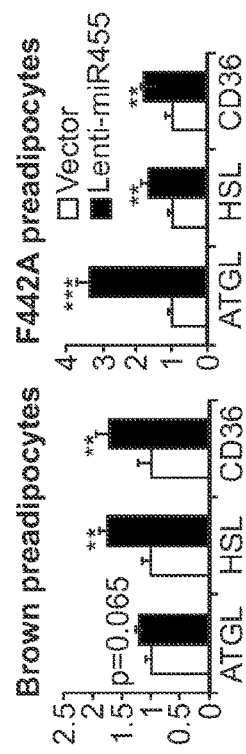
Figure 7A:
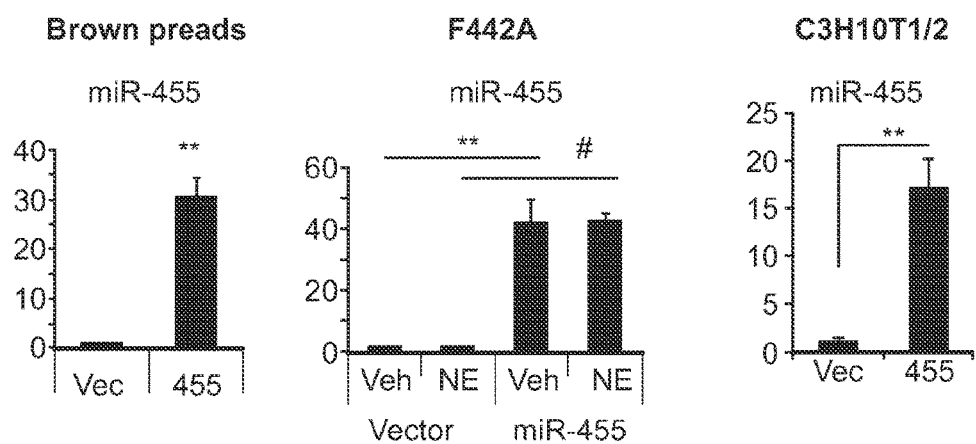
FIG. 7 shows a. Overexpression of miR-455 by lentiviral vector in brown preadipocytes, 3T3-F442A and C3H10T1/2 cells, as assayed by RT-Q-PCR on Day 0. b. Overexpression of miR-455 upregulated mitochondria gene expression in the three types of cells on Day 0.
Figure 7B:
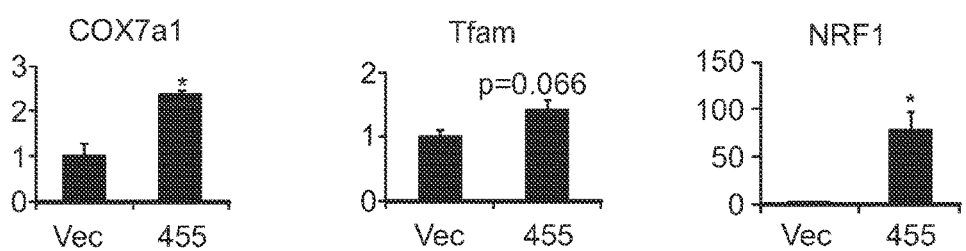
Figure 9:
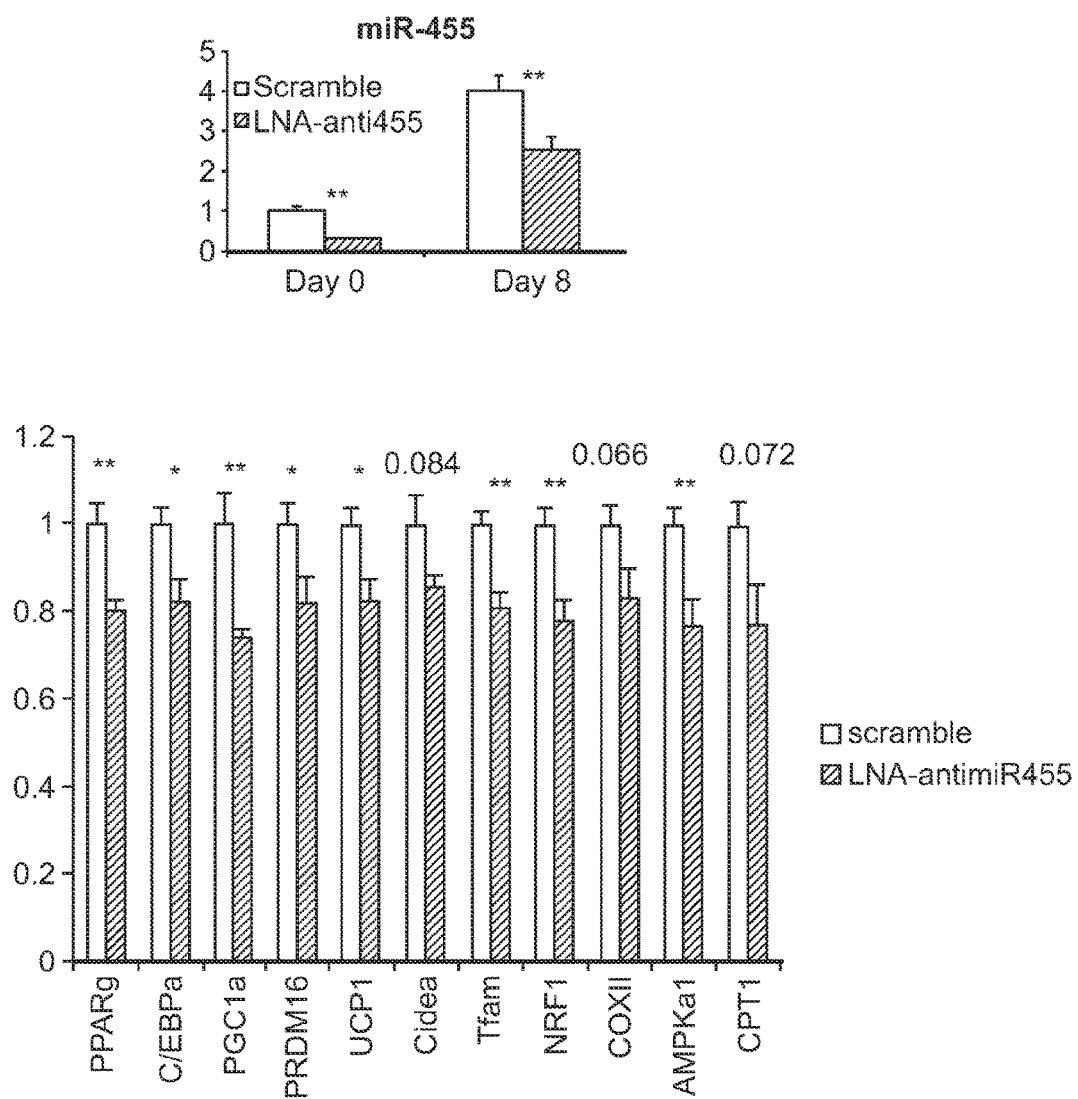
FIG. 9 shows LNA-mediated Knockdown of miR-455 in Brown preadipocytes. Brown Preadipocytes were transfected with scramble or anti-455 LNAs at 80% confluency. 2 days after transfection, the cells reached 100% confluency, and were induced to differentiation by standard differentiation protocol (0.5 uM Dex, 0.5 mM IBMX, 20 nM insulin, 1 nM T3), followed by incubation in 20 nM insulin+1 nM T3 throughout differentiation process. On Day 8, cells were harvested and analyzed for miR-455 and gene expression. (*p<0.05, **p<0.01. p values were shown above the column).

The result that miR-455 induced the commitment and differentiation of multipotent progenitor cells and white preadipocytes along brown adipogenic lineage both in vitro and in vivo suggested that miR-455 expression should have triggered gene expression profile in the cells favoring brown adipogenesis prior to adipogenic induction. To access this hypothesis, we examine the gene expression prior to differentiation induction (day 0) in all the 3 type of cells used in vitro. In all the 3 types of undifferentiated cells, miR-455 overexpression significantly induced PGC1α and some mitochondrial gene expression, independent of adipocyte differentiation (FIG. 2g) and some mitochondrial gene (FIG. 7b) expression, independent of adipocyte differentiation. PGC1α is the driving factor for mitochondria biogenesis (Z. Wu, et al., "Mechanisms controlling mitochondrial biogenesis and respiration through the thermogenic coactivator PGC-1," Cell 98(1), 115 (1999)) and UCP1 expression (W. Cao, et al., "p38 mitogen-activated protein kinase is the central regulator of cyclic AMP-dependent transcription of the brown fat uncoupling protein 1 gene," Mol. Cell Biol. 24(7), 3057 (2004); P. Puigserver, et al., "A cold-inducible coactivator of nuclear receptors linked to adaptive thermogenesis," Cell 92(6), 829 (1998)). Thus, the observed upregulation of PGC1α could explain miR-455-induced UCP1 expression and brown adipogenesis. Indeed, miR-455 overexpression in C3H10T1/2 cells induced mitochondrial biogenesis by over 2 folds as indicated by the DNA content ratio between mitochondria gene COXII and nuclear gene globin (FIG. 2h). Consistent with this, miR-455 overexpression also significantly increased both basal and maximum respiratory capacity of C3H10T1/2 cells in the bioenergetics analysis by Seahorse (FIG. 2h). Interestingly, miR-455 overexpression in both brown and white (F442A) preadipocytes induced expression of genes involved in lipolysis (such as ATGL and HSL) and fatty acid mobilization (such as CD36) and lipolysis (such as ATGL and HSL) (FIG. 2i). Adipocyte-specific ATGL-knockout mice showed conversion of BAT to WAT, revealing the requirement of ATGL-catalyzed lipolysis in the maintenance of a BAT phenotype (M. Ahmadian, et al., "Desnutrin/ATGL is regulated by AMPK and is required for a brown adipose phenotype," Cell Metab 13(6), 739 (2011)). Therefore, the upregulation of lipolysis and fatty acid mobilization genes could also contribute to miR-455-mediated brown adipogeneis.

miRNAs work through suppressing their target gene expression. To identify miR-455 targets, the target prediction tools TargetScan (www.targetscan.org) and miRTarget2 (mirdb.org) were used. These tools each predicted about 200 miR-455 targets, of which Runx1t1, necdin and HIF1an (hypoxia-inducible factor 1, alpha subunit inhibitor) were among the top predicted targets. They each contain at least one highly conserved target perfectly matching the 7-mer seed region of miR-455 (FIG. 8), suggesting an evolutionally conserved function of these miR-455/target pairs. Runx1t1 (J. J. Rochford, et al., "ETO/MTG8 is an inhibitor of C/EBPbeta activity and a regulator of early adipogenesis," Mol. Cell Biol. 24(22), 9863 (2004)) and necdin (Y. H.

Tseng, et al., "Prediction of preadipocyte differentiation by gene expression reveals role of insulin receptor substrates and necdin," Nat. Cell Biol. 7(6), 601 (2005)) were reported to be adipogenic inhibitors. Interestingly, it was reported that HIF1an-null mice had reduced body mass due to decreased adiposity in WAT, elevated metabolic rate and heat production due to increased UCP1 and PGC1α expression in interscapular BAT, and improved glucose and lipid homeostasis (N. Zhang, et al., "The asparaginyl hydroxylase factor inhibiting HIF-1alpha is an essential regulator of metabolism," Cell Metab 11(5), 364 (2010)). HIF1an, an asparaginal hydroxylase, was able to modulate multiple key biological factors (including HIF1α (D. Lando, et al., "FIH-1 is an asparaginyl hydroxylase enzyme that regulates the transcriptional activity of hypoxia-inducible factor," Genes Dev. 16(12), 1466 (2002)), IκB (I. L. Devries, et al., "Consequences of IkappaB alpha hydroxylation by the factor inhibiting HIF (FIH)," FEBS Lett. 584(23), 4725 (2010)), Notch (X. Zheng, et al., "Interaction with factor inhibiting HIF-1 defines an additional mode of cross-coupling between the Notch and hypoxia signaling pathways," Proc. Natl. Acad. Sci. U.S.A. 105(9), 3368 (2008)) through β-hydroxylation of asparaginyl residues as an important regulatory mechanism. Our observed broad effects of miR-455 could not be explained by a single transcriptional factor, but rather appeared to be a metabolic consequence. It is likely that Runx1t1 and necdin could act as the gate keepers to allow multipotent progenitors to enter into adipogenic lineage when being suppressed by miR-455, while HIF1an could be the gene triggering the observed divergent metabolic effects leading to UCP1 expression and browning when suppressed by miR-455.

Figure 4A:
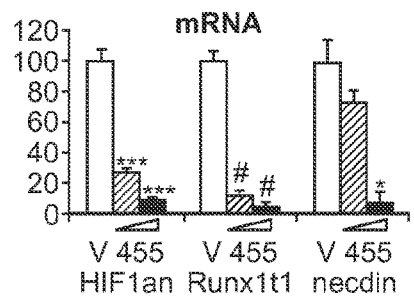
FIG. 4 shows molecular mechanism of miR-455-induced brown adipogenesis. a, Target gene mRNAs were quantified by Q-RT-PCR in brown preadipocytes expressing different level of miR-455 (v=vector). b, RNA-ChIP assays were carried out in brown preadipocytes using control Normal Immunoglobulin (Ig) or anti-Ago2 antibody. Co-precipitated miR-455 and target gene mRNA were quantified by Q-RT-PCR. c-e, 3'UTR of target genes (HIF1an, Runx1t1 and necdin) were cloned downstream of a luciferase Reporter. The reporter plasmids were transfected in brown preadipocytes along with different dosages of either scramble oligos(scr), miR-455 mimics or anti-miR-455, and analyzed for luciferase activity. Shown were Mean±SEM of a representative of 2 to 5 independent experiments. (*p<0.05, p<0.01, *p<0.001, #p<0.0001; n.d., none detectable).
Figure 4B:
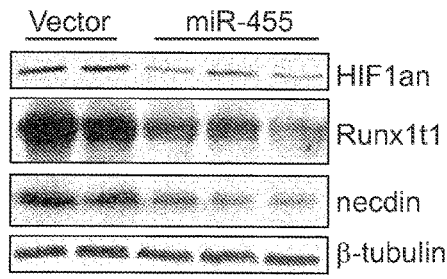
Figure 4C:
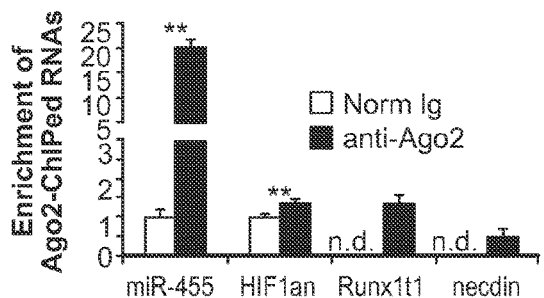

To address this, it was first examined whether the three genes were miR-455 targets. Since miR-455 is specifically expressed in brown adipocytes, we used brown preadipocytes as the natural cellular system for this test. miRNAs suppress gene expression by targeting their 3'UTR, leading to mRNA cleavage and/or translational inhibition. We first quantified the expression of Runx1t1, necdin and HIF1an in brown preadipocytes overexpressing miR-455 on both mRNA and protein levels. Both mRNA (FIG. 4a) and protein levels (FIG. 4b) of the three genes were markedly suppressed by miR-455 compared to control. Importantly, mRNA suppression by miR-455 was achieved in a dose-dependent manner (FIG. 4a). miRNAs inhibit their target gene expression by targeting on their 3'UTR, which induces protein translational suppression and/or mRNA degradation (S. Djuranovic, A. Nahvi, and R. Green, "A parsimonious model for gene regulation by miRNAs," Science 331(6017), 550 (2011)). Although it is debatable as to which of the two mechanisms is prevalent, and even though the present invention is not limited by theory, data from Dr. Bartel's lab using ribosome-profiling technique clearly demonstrated that mRNA degradation accounted for the majority of gene expression suppression by miRNAs (H. Guo, et al., "Mammalian microRNAs predominantly act to decrease target mRNA levels," Nature 466(7308), 835 (2010)). Consistent with this notion, our data shows that mRNA cleavage is the major mechanism for miR-455-mediated gene suppression.

miRNAs interact with their target 3'UTR in the RISC (RNA-induced silencing complex) platform. Ago2 is the central player in RISC responsible for miRNA integration and mRNA cleavage (N. T. Schirle and I. J. MacRae, "The crystal structure of human Argonaute2," Science 336(6084), 1037 (2012)). Therefore, next we performed RNA-ChIP assay, where we precipitated Ago2 using anti-Ago2 antibody, and then quantified co-precipitated miR-455 and their target mRNAs to detect the direct physical interaction between miR-455 and their target mRNAs. Consistent with the 20× fold enrichment of miR-455 in anti-Ago2 precipitates over that in Normal-Ig precipitates, HIF1an, Runx1t1 and necdin mRNA were all significantly enriched in anti-Ago2 precipitates compared to that in normal-Ig precipitates (FIG. 4c). The fold discrepancy of enrichment between miR-455 and its target genes could be because the majority of the target mRNAs integrated in RISC had been cleaved by miR-455.

Figure 4D:
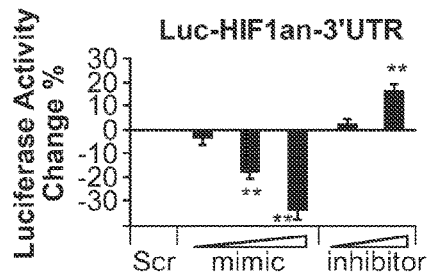
Figure 4E:
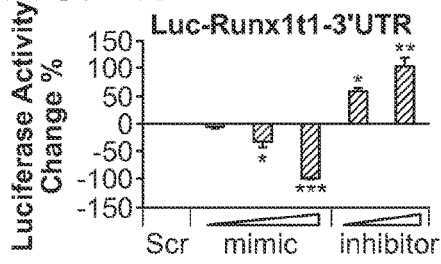
Figure 4F:
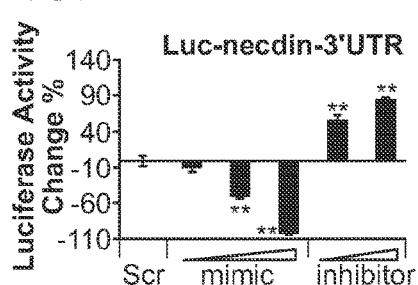
Figure 12:
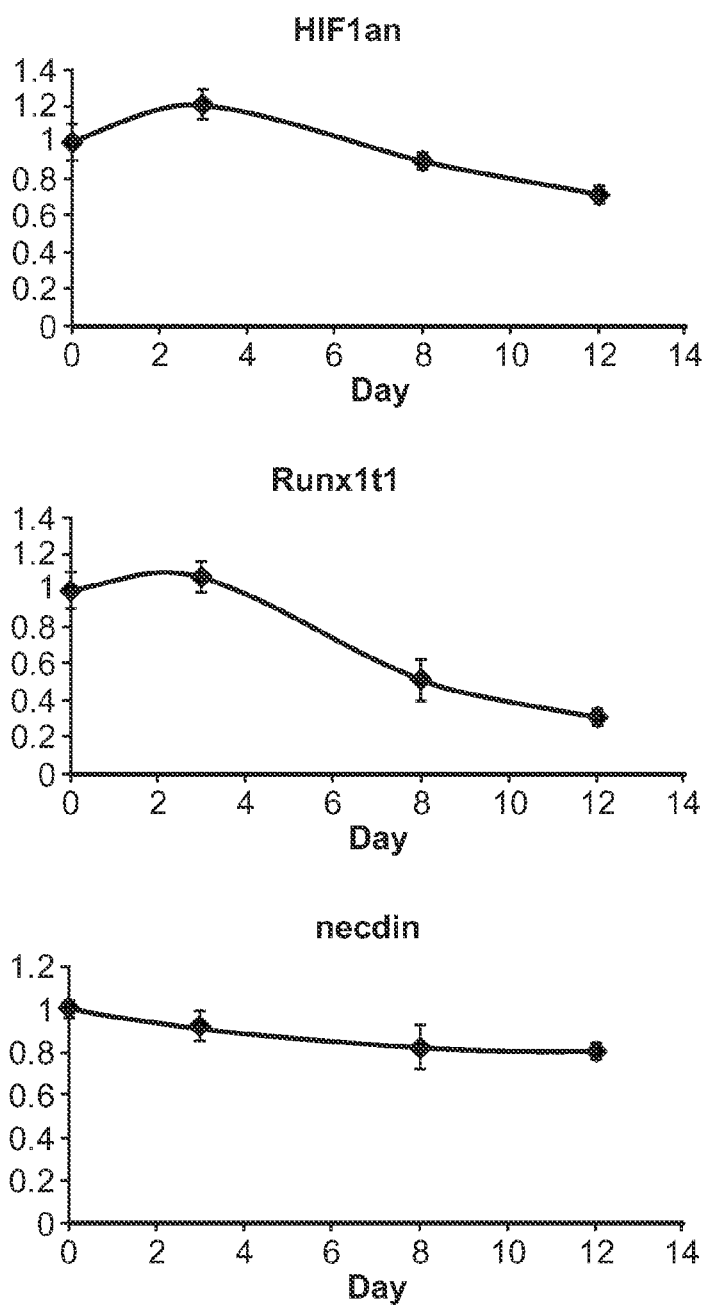
FIG. 12 shows expression of miR-455 target genes were downregulated during brown adipocyte differentiation. Brown preadipocytes were induced to differentiation by standard differentiation protocol (see methods). mRNA level of target genes were quantified by RT-Q-PCR.

Third, a reporter construct containing luciferase cDNA linked to 3'UTR sequences of the target mRNAs was generated. When the reporter constructs and miR-455 mimics or inhibitors were co-transfected into brown preadipocytes, miR-455 mimics suppressed and miR-455 inhibitor activated luciferase activities significantly in a dose-dependent manner, while Scramble (Scr) did not have any effect (FIG. 4d). Thus, miR-455 suppressed its target gene expression by specifically targeting on the 3'UTR of the genes. Taken together, the present invention demonstrates that Runx1t1, necdin and HIF1an were genuine targets of miR-455. The discovery of multiple targets of miR-455 in brown adipogenic signaling is consistent with the idea of mirBridge that the target sites of a miRNA could be enriched in multiple components of the same signaling pathway. The expression of these three target genes were downregulated during brown adipocyte differentiation (FIG. 12), and also suppressed by cold exposure (FIG. 13), consistent with the upregulation of miR-455 during brown adipocyte differentiation (FIG. 1c, d) and by cold exposure (FIG. 1e), which highlights the function of miR-455 for brown adipogenesis.

Figure 14A:
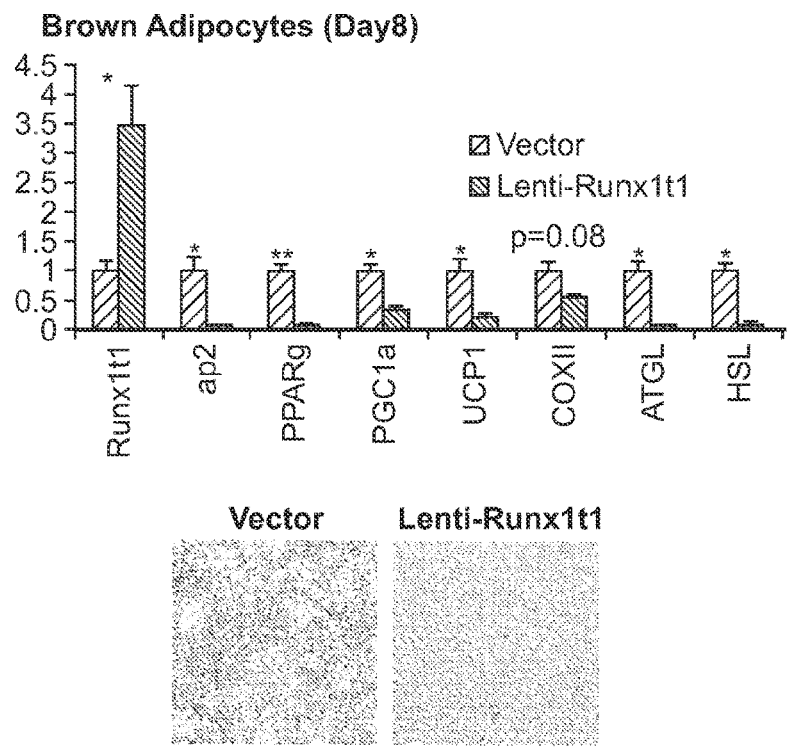
FIG. 14 shows a. Overexpression of Runx1t1 inhibited brown adipocyte differentiation. Runx1t1 was overexpressed in brown preadipocytes via lentiviral delivery, empty vector was used as control. Stably transduced cells were selected and pooled. On Day 8, gene expressions were analyzed by Q-RT-PCR, and cells were stained by Oil Red O. b, Overexpression of HIF1an blocked miR-455 in inducing brown adipogenic activator PGC1α prior to differentiation. A non-3'UTR HIF1an transgene was overexpressed on top of miR-455 in brown preadipocytes. Empty vectors were used as controls. On Day 0, miR-455 and gene expressions were analyzed by Q-RT-PCR. (*, p<0.05).
Figure 14B:
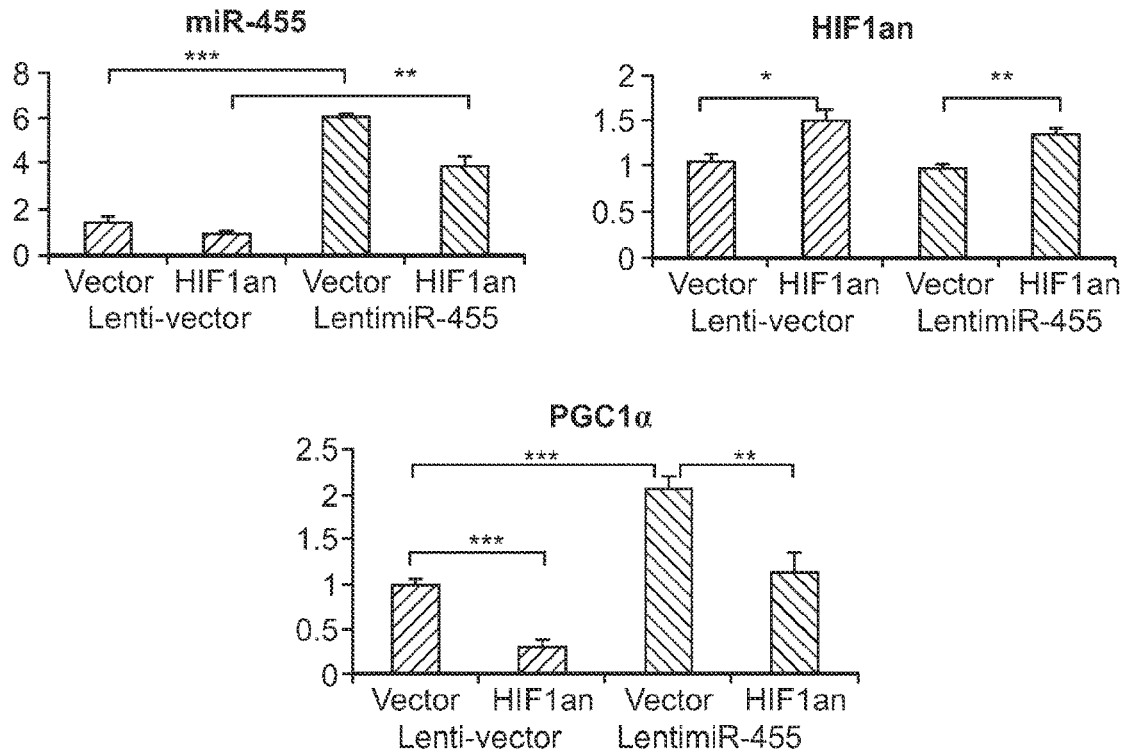
Figure 15:
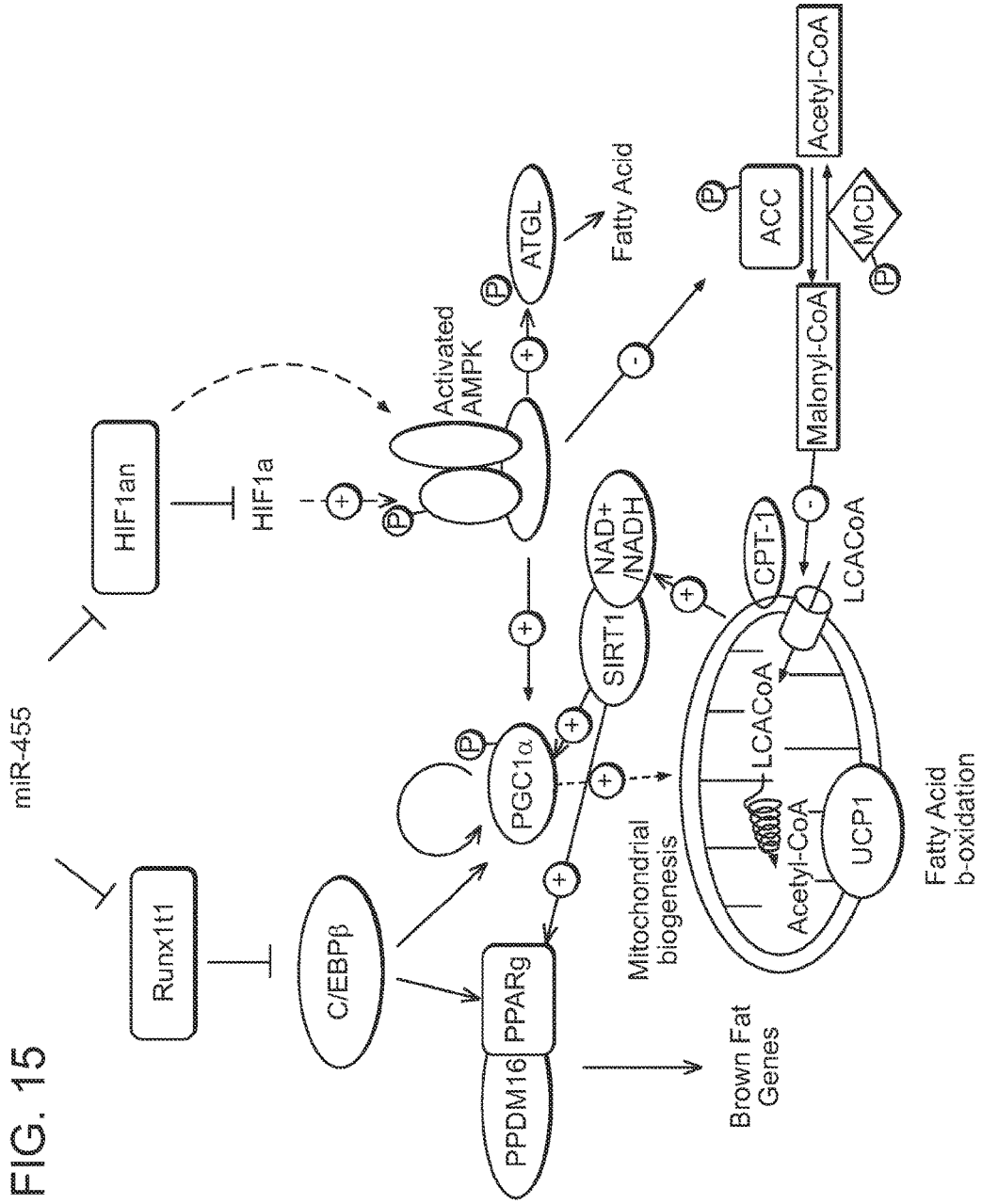
FIG. 15 shows a model of miR-455-mediated brown adipogenesis.

To further verify the function of HIF1an in brown adipogenesis, HIF1an gene, which lacked its native 3'UTR and therefore was miR-455 insensitive, was overexpressed on top of miR-455. Overexpression of HIF1an in miR-455-brown preadipocytes completely blocked miR-455 in inducing the expression of brown adipogenic activator PGC1α (FIG. 14b). These data demonstrate that suppression of HIF1an is required for PGC1α expression and brown adipogenesis.

Figure 5A:
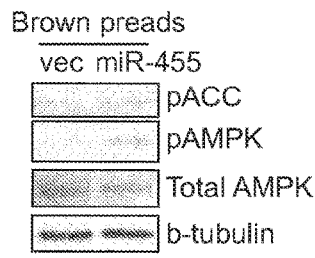
FIG. 5 shows miR-455 suppressed HIF1an and Runx1t1 protein and activated AMPKa1. a, Western blot analysis of brown preadiocytes (Day 0, before induction of differentiation) transduced by vector (vec) or miR-455 lentivirus. b, Cell lysates of brown preadipocytes (Day 0) were immunoprecipitated (IP) with control Normal Immunoglobulin (Ig) or anti-HIF1an antibody, and blotted with anti-HIF1an and anti-AMPKa antibodies. 10% of cell lysates used for IP were blotted as input. c, Equal amount of AMPKa1 was first Immunoprecipitated using anti-AMPKa1 antibody from brown preadipocytes (Day 0) or mature adipocytes (Day 7) transduced with different lentiviruses and treated with vehicle (DMSO) or clioquinol (CQ), and then quantified for AMPKa1 activity.

Runx1t1 suppresses white adipogenesis through interacting with C/EBPβ and inhibiting its transcriptional activity (J. J. Rochford, et al., "ETO/MTG8 is an inhibitor of C/EBPbeta activity and a regulator of early adipogenesis," Mol. Cell Biol. 24(22), 9863 (2004)). It is confirmed herein that overexpression of Runx1t1 completely blocked brown adipocyte differentiation (FIG. 14a). Previously we showed that necdin blocked brown adipogenesis by interacting with E2Fs and blunting its capability to activate PPARγ1 promoter (Y. H. Tseng, et al., "Prediction of preadipocyte differentiation by gene expression reveals role of insulin receptor substrates and necdin," Nat. Cell Biol. 7(6), 601 (2005)). But, how does HIF1an suppress brown adipocyte differentiation and/or function? Our results herein showed that miR-455 triggered a broad range effects from brown adipogenic transcriptional regulation, mitochondria biogenesis to lipolysis and fatty acid mobilization, suggesting a model of metabolic regulation. One candidate enzyme that can lead to such a broad range of regulation is AMPK. AMPK activity increased during brown adipocyte differentiation, and siRNA knockdown of AMPK inhibited brown adipogenesis (R. Vila-Bedmar, M. Lorenzo, and S. Fernandez-Veledo, "Adenosine 5'-monophosphate-activated protein kinase-mammalian target of rapamycin cross talk regulates brown adipocyte differentiation," Endocrinology 151 (3), 980 (2010)). AMPK is also able to directly phosphorylate PGC1α (S. Jager, et al., "AMP-activated protein kinase (AMPK) action in skeletal muscle via direct phosphorylation of PGC-1alpha," Proc. Natl. Acad. Sci. U.S.A. 104(29), 12017 (2007)) to generate the primary signal for its further deacetylation by SIRT1, which then fully activate its own promoter to boost a positive feedback transcriptional regulation (C. Canto, et al., "AMPK regulates energy expenditure by modulating NAD+ metabolism and SIRT1 activity," Nature 458(7241), 1056 (2009)). The upregulated PGC1α expression accounts for miR-455-induced mitochondria biogenesis and activity. AMPK has been shown to induce mitochondrial β-oxidation via activating ACC/Malonyl-CoA/CPT1 pathway in adipocytes (M. P. Gaidhu, et al., "Prolonged AICAR-induced AMP-kinase activation promotes energy dissipation in white adipocytes: novel mechanisms integrating HSL and ATGL," J. Lipid Res. 50(4), 704 (2009); M. P. Gaidhu, et al., "Chronic AMP-kinase activation with AICAR reduces adiposity by remodeling adipocyte metabolism and increasing leptin sensitivity," J. Lipid Res. 52(9), 1702 (2011)). SIRT1 activity is also under the direct modulation by mitochondria activity which provides NAD+/NADH, the substrate for SIRT1 (C. Canto, et al., "AMPK regulates energy expenditure by modulating NAD+ metabolism and SIRT1 activity," Nature 458(7241), 1056 (2009)). AMPK can also directly activate ATGL through Ser$^{406}$ phosphorylation (M. Ahmadian, et al., "Desnutrin/ATGL is regulated by AMPK and is required for a brown adipose phenotype," Cell Metab 13(6), 739 (2011)), the primary enzyme regulating lipolysis in adipocytes. The lipolytic products in turn act as the ligands to activate PPARα and PPARβ which can transcriptionally activate PGC1α and UCP1 in brown adipocytes (E. P. Mottillo, et al., "Lipolytic products activate peroxisome proliferator-activated receptor (PPAR) alpha and delta in brown adipocytes to match fatty acid oxidation with supply," J. Biol. Chem. 287(30), 25038 (2012)). Indeed, overexpression of miRNA-455 induced AMPKα phophorylation, as well as the phosphorylation of its downstream substrate ACC (FIG. 5a).

Figure 5B:
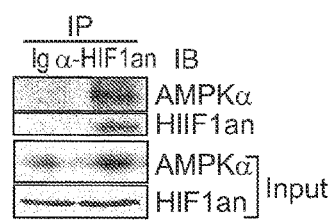
Figure 5C:
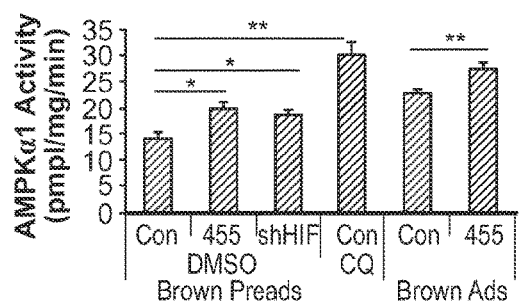

Although the present invention is not limited by theory, it is believed that the suppression of HIF1an leads to AMPK activation as follows. HIF1an is an asparaginyl hydroxylase which has multiple substrates. The conventional model for enzyme/substrate reaction is that they physically interact with each other. Therefore, an immunoprecipitation (IP) assay was performed to detect the interaction between HIF1an and AMPK. Specific anti-HIF1an antibody efficiently co-precipitated AMPKα in brown preadipocytes (FIG. 5b), suggesting that HIF1an could physically interact with AMPKα and therefore inhibits the activity of AMPKα in undifferentiated preadipocytes. AMPKα subunit is the catalytic subunit of AMPK, and has two isoforms, AMPKα1, α2, with AMPKα1 being the dominant subunit isoform in BAT (J. D. Mulligan, et al., "Upregulation of AMPK during cold exposure occurs via distinct mechanisms in brown and white adipose tissue of the mouse," J. Physiol 580(Pt. 2), 677 (2007)) and WAT (M. Daval, et al., "Antilipolytic action of AMP-activated protein kinase in rodent adipocytes," J. Biol. Chem. 280(26), 25250 (2005); I. P. Salt, J. M. Connell, and G. W. Gould, "5-aminoimidazole-4-carboxamide ribonucleoside (AICAR) inhibits insulin-stimulated glucose transport in 3T3-L1 adipocytes," Diabetes 49(10), 1649 (2000)). To further verify this observation and to distinguish which AMPKα subunit interacts with HIF1an, AMPKα proteins were precipitated using isoform-specific AMPKα antibodies from both preadipocytes and differentiated mature adipocytes, and AMPK activities were measured. Both miR-455 overexpression and shRNA-mediated HIF1an knockdown significantly induced AMPKα1 activity in brown preadipocytes compared to control (FIG. 5c). Overexpression of miR-455 also significantly increased AMPKα1 activity in mature brown adipocytes (FIG. 5c). Several HIF1an specific inhibitors have been developed, among which Clioquinol (CQ) binds to the active site of HIF1an to block its hydroxylase activity (H. Moon, et al., "Crystal structures of human FIH-1 in complex with quinol family inhibitors," Mol. Cells 29(5), 471 (2010)). Five hours of CQ treatment of brown preadipocytes induced a 2-fold AMPKα1 activation relative to DMSO treatment (FIG. 5c). miR-455, siRNA-HIF1an or CQ treatment did not have effect on AMPKα2 activity (data not shown). It is important to note that short-term cold exposure induced miR-455 expression (FIG. 1e), but only chronic cold exposure selectively upregulated AMPKα1 (not AMPKα2) activity in BAT (J. D. Mulligan, et al., "Upregulation of AMPK during cold exposure occurs via distinct mechanisms in brown and white adipose tissue of the mouse," J. Physiol 580(Pt. 2), 677 (2007)), suggesting that miR-455 could selectively mediate β-adrenergic AMPKα1 activation. These data confirmed that interaction between HIF1an and AMPKα1 inhibited AMPKα1 activity. Thus, the miR-455-induced brown adipogenesis, mitochondrial biogenesis and lipolysis could attribute to the regulation by the HIF1an-AMPKα1 axis. The mouse AMPKα1 contains 18 asparaginyl residues, of which 16 residues are highly conserved across species.

Taken together, the present invention demonstrates that brown-fat specific miR-455 promotes brown adipose development by targeting on key brown adipogenic signaling molecules. Importantly, we discovered a novel interaction between HIF1an and AMPKα1, where hydroxylation of AMPKα1 by HIF1an inhibits AMPKα1 activity. Thus, miR-455-activated AMPKα1 acts as a metabolic trigger to initiate mitochondria biogenesis, PGC1α induction and brown adipogenesis. Concomitantly, suppression of Runx1t1 and necdin by miR-455 allows the cells to enter adipogenic process. Thus, the present invention has uncovered a novel miRNA-initiated signaling network leading to mitochondria biogenesis and brown adipogenesis.

What is claimed is:

1. A method of regulating Brown Adipose Tissue (BAT) activation and differentiation in a subject, the method comprising contacting one or more cells in the subject by administering to the subject a composition comprising one or more exogenous miRNA-455 selected from the group consisting of [SEQ ID NOs: 1-4], the cells being selected from the group consisting of brown adipose cells, white adipose cells and preadipocytes and following said administration of said miRNA-455 to the subject the amount of BAT and/or BAT activity in the subject increases.

2. The method of claim 1, wherein the upregulation of BAT comprises increasing the thermogenic activity of BAT.

3. The method of claim 1, wherein the upregulation of BAT comprises increasing the amount of BAT in the subject.

4. The method of claim 1, wherein said subject is overweight or obese.

5. The method of claim 1, wherein said subject has diabetes.

6. The method of claim 5, wherein said diabetes is selected from type 1 and type 2 diabetes.

7. The method of claim 1, wherein said composition comprising exogenous miRNA-455 additionally comprises a pharmacologically acceptable carrier.

8. A method of treating obesity in a subject, the method comprising contacting one or more cells in the subject by administering to the subject a composition comprising one or more exogenous miRNA-455 selected from the group consisting of [SEQ ID NOs: 1-4], wherein the cells are selected from the group consisting of brown adipose tissue, white adipose tissue and preadipocytes and following said administration of said miRNA-455 to the subject the amount of BAT and/or BAT activity in the subject increases.

9. The method of claim 8, wherein the treatment of obesity comprises increasing the thermogenic activity of BAT.

10. The method of claim 8, wherein the treatment of obesity comprises increasing the amount of BAT in the subject.

11. The method of claim 8, wherein said subject has diabetes.

12. The method of claim 11, wherein said diabetes is selected from type 1 and type 2 diabetes.

13. The method of claim 1, wherein said method further comprises detecting an increase in thermogenic activity of BAT in the subject.

14. The method of claim 1, wherein said method further comprises detecting an increase in the amount of BAT in the subject.

15. The treatment of claim 8, wherein said treatment further comprises monitoring said treatment by detecting an increase in thermogenic activity of BAT in the subject.

16. The treatment of claim 8, wherein said treatment further comprises monitoring said treatment by detecting an increase in the amount of BAT in the subject.

17. The method of claim 1, wherein the subject is monitored for BAT activation and/or differentiation.

18. The method of claim 8, wherein the subject is monitored for BAT activation and/or differentiation.

* * * * *

SEQUENCE LISTING

```
<160> NUMBER OF SEQ ID NOS: 17

<210> SEQ ID NO 1
<211> LENGTH: 21
<212> TYPE: RNA
<213> ORGANISM: Homo sapiens

<400> SEQUENCE: 1
gcaguccaug ggcauauaca c                                              21
```

```
<210> SEQ ID NO 2
<211> LENGTH: 21
<212> TYPE: RNA
<213> ORGANISM: Mus musculus

<400> SEQUENCE: 2
gcaguccacg ggcauauaca c                                              21

<210> SEQ ID NO 3
<211> LENGTH: 22
<212> TYPE: RNA
<213> ORGANISM: Rattus norvegicus

<400> SEQUENCE: 3
gcaguccacg ggcauauaca cu                                             22

<210> SEQ ID NO 4
<211> LENGTH: 22
<212> TYPE: RNA
<213> ORGANISM: Gallus gallus

<400> SEQUENCE: 4
ugcaguccau gggcauauac ac                                             22

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gcaguccacg ggcauauaca c                                              21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
taugugccuu uggacuacau cg                                             22

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tatgcccgtg gactg                                                     15

<210> SEQ ID NO 8
<211> LENGTH: 23
<212> TYPE: RNA
<213> ORGANISM: Mus musculus

<400> SEQUENCE: 8
```

-continued gcacgcugca cuuaauggac ugg                                    23

<210> SEQ ID NO 9
<211> LENGTH: 21
<212> TYPE: RNA
<213> ORGANISM: Mus musculus

<400> SEQUENCE: 9
gcaguccacg ggcauauaca c                                      21

<210> SEQ ID NO 10
<211> LENGTH: 23
<212> TYPE: RNA
<213> ORGANISM: Mus musculus

<400> SEQUENCE: 10
gcuuacagcg ccccauggac uga                                    23

<210> SEQ ID NO 11
<211> LENGTH: 21
<212> TYPE: RNA
<213> ORGANISM: Mus musculus

<400> SEQUENCE: 11
gcaguccacg ggcauauaca c                                      21

<210> SEQ ID NO 12
<211> LENGTH: 20
<212> TYPE: RNA
<213> ORGANISM: Mus musculus

<400> SEQUENCE: 12
auccaugugg aauggacuga                                        20

<210> SEQ ID NO 13
<211> LENGTH: 21
<212> TYPE: RNA
<213> ORGANISM: Mus musculus

<400> SEQUENCE: 13
gcaguccacg ggcauauaca c                                      21

<210> SEQ ID NO 14
<211> LENGTH: 20
<212> TYPE: RNA
<213> ORGANISM: Mus musculus

<400> SEQUENCE: 14
acugauuuga acuggacugu                                        20

<210> SEQ ID NO 15
<211> LENGTH: 21
<212> TYPE: RNA
<213> ORGANISM: Mus musculus

<400> SEQUENCE: 15
gcaguccacg ggcauauaca c                                      21

<210> SEQ ID NO 16
<211> LENGTH: 23
<212> TYPE: RNA
<213> ORGANISM: Mus musculus

```
<400> SEQUENCE: 16
uuuuuuuucc uuaguuggac ugu                                              23

<210> SEQ ID NO 17
<211> LENGTH: 21
<212> TYPE: RNA
<213> ORGANISM: Mus musculus

<400> SEQUENCE: 17
gcaguccacg ggcauauaca c                                                21
```